US006979567B2

(12) United States Patent
Herron et al.

(10) Patent No.: US 6,979,567 B2
(45) Date of Patent: Dec. 27, 2005

(54) APPARATUS AND METHODS FOR MULTI-ANALYTE HOMOGENEOUS FLUORO-IMMUNOASSAYS

(75) Inventors: James N. Herron, Salt Lake City, UT (US); Douglas A. Christensen, Salt Lake City, UT (US); Hsu-Kun Wang, Salt Lake City, UT (US); Karin Caldwell, Salt Lake City, UT (US); Vera Janatová, Prague (CZ); Shao-Chie Huang, Salt Lake City, UT (US)

(73) Assignee: BioCentrex, LLC, Culver City, CA (US)

( * ) Notice: Subject to any disclaimer, the term of this patent is extended or adjusted under 35 U.S.C. 154(b) by 327 days.

(21) Appl. No.: 10/008,339

(22) Filed: Nov. 13, 2001

(65) Prior Publication Data

US 2002/0160535 A1 Oct. 31, 2002

Related U.S. Application Data

(63) Continuation of application No. 09/516,307, filed on Mar. 1, 2000, now Pat. No. 6,316,274, which is a division of application No. 08/979,582, filed on Nov. 26, 1997, now abandoned, which is a continuation-in-part of application No. 08/748,687, filed on Nov. 13, 1996, now Pat. No. 5,919,712, which is a division of application No. 08/263,522, filed on Jun. 22, 1994, now Pat. No. 5,677,196, which is a continuation of application No. 08/110,169, filed on Aug. 20, 1993, now Pat. No. 5,516,703, and a continuation of application No. 08/071,579, filed on Jun. 2, 1993, now abandoned, which is a continuation of application No. 08/064,608, filed on May 18, 1993, now Pat. No. 5,512,492.

(51) Int. Cl.$^7$ .............................................. C12M 3/00
(52) U.S. Cl. ...................... 435/287.1; 422/55; 422/57; 422/58; 422/82.05; 422/82.08; 422/82.11; 435/287.2; 435/287.9; 435/288.5; 435/288.7; 435/808; 436/164; 436/165; 436/514; 436/518; 436/527; 436/531; 436/805; 436/807; 385/12; 385/129; 385/130; 356/418

(58) Field of Search .................. 422/55, 57, 58, 422/82.05, 82.08, 82.11; 435/287.1, 287.2, 287.9, 288.5, 288.7, 808; 436/164, 165, 518, 527, 531, 805, 807, 514; 385/12, 129, 130; 356/418

(56) References Cited

U.S. PATENT DOCUMENTS 3,939,350 A 2/1976 Kronick et al.

(Continued)

FOREIGN PATENT DOCUMENTS

EP 0 478 137 1/1992

(Continued)

OTHER PUBLICATIONS

Carlsson, "Protein Thiolation and Reversible Protein-Protein Conjugation", *Biochem J.*, 173, pp. 723–737, 1978.

(Continued)

*Primary Examiner*—Christopher L. Chin
(74) *Attorney, Agent, or Firm*—TraskBritt, PC

(57) ABSTRACT

Methods and apparatus for evanescent light fluoroimmunoassays are disclosed. The apparatus employs a planar waveguide with an integral semicylindrical lens, and has multi-analyte features and calibration features, along with improved evanescent field intensity. A preferred embodiment of the biosensor and assay method has patches of capture molecules, each specific for a different analyte disposed adjacently within a single reservoir. The capture molecules are immobilized to the patches on the waveguide surface by site-specific coupling of thiol groups on the capture molecules to photo-affinity crosslinkers, which in turn are coupled to the waveguide surface or to a nonspecific binding-resistant coating on the surface. The patches of different antibodies are produced by selectively irradiating a portion of the waveguide surface during the process of coupling the photo-affinity crosslinkers, the selective irradiation involving a mask, a laser light source, or the like.

30 Claims, 14 Drawing Sheets

U.S. PATENT DOCUMENTS

| | | | |
|---|---|---|---|
| 3,959,078 | A | 5/1976 | Guire |
| 4,050,895 | A | 9/1977 | Hardy et al. |
| 4,166,105 | A | 8/1979 | Hirschfeld |
| 4,235,869 | A | 11/1980 | Schwarzberg |
| 4,264,766 | A | 4/1981 | Fischer |
| 4,298,685 | A | 11/1981 | Parikh et al. |
| 4,429,008 | A | 1/1984 | Martin et al. |
| 4,447,546 | A | 5/1984 | Hirschfeld |
| 4,450,231 | A | 5/1984 | Ozkan |
| 4,558,014 | A | 12/1985 | Hirschfeld et al. |
| 4,562,157 | A | 12/1985 | Lowe et al. |
| 4,596,723 | A | 6/1986 | Kaufman et al. |
| 4,627,445 | A | 12/1986 | Garcia et al. |
| 4,708,871 | A | 11/1987 | Geysen |
| 4,722,906 | A | 2/1988 | Guire |
| 4,775,637 | A | 10/1988 | Sutherland et al. |
| 4,806,312 | A | 2/1989 | Greenquist |
| 4,810,658 | A | 3/1989 | Shanks et al. |
| 4,820,649 | A | 4/1989 | Kawaguchi et al. |
| 4,826,759 | A | 5/1989 | Guire et al. |
| 4,852,967 | A | 8/1989 | Cook et al. |
| RE33,064 | E | 9/1989 | Carter et al. |
| 4,880,752 | A | 11/1989 | Keck et al. |
| 4,909,990 | A | 3/1990 | Block et al. |
| 4,973,493 | A | 11/1990 | Guire |
| 4,978,503 | A | 12/1990 | Shanks et al. |
| 4,979,959 | A | 12/1990 | Guire |
| 4,997,278 | A | 3/1991 | Finlan et al. |
| 5,002,582 | A | 3/1991 | Guire et al. |
| 5,006,333 | A | 4/1991 | Saifer et al. |
| 5,006,716 | A | 4/1991 | Hall |
| 5,043,278 | A | 8/1991 | Nagaoka et al. |
| 5,061,857 | A | 10/1991 | Thompson et al. |
| 5,071,216 | A | 12/1991 | Sullivan |
| 5,071,217 | A | 12/1991 | Birch |
| 5,073,484 | A | 12/1991 | Swanson et al. |
| 5,081,012 | A | 1/1992 | Flanagan et al. |
| 5,096,807 | A | 3/1992 | Leaback |
| 5,135,876 | A | 8/1992 | Andrade et al. |
| 5,156,976 | A | 10/1992 | Slovacek et al. |
| 5,166,515 | A | 11/1992 | Attridge |
| 5,168,537 | A | 12/1992 | Rajasekharan et al. |
| 5,182,216 | A | 1/1993 | Clayton et al. |
| 5,186,897 | A | 2/1993 | Eason et al. |
| 5,192,502 | A | 3/1993 | Attridge et al. |
| 5,217,492 | A | 6/1993 | Guire et al. |
| RE34,394 | E | 9/1993 | Bunting |
| 5,242,828 | A | 9/1993 | Bergstrom et al. |
| 5,248,620 | A | 9/1993 | Sluka et al. |
| 5,258,041 | A | 11/1993 | Guire et al. |
| 5,263,992 | A | 11/1993 | Guire |
| 5,344,784 | A | 9/1994 | Attridge |
| 5,380,668 | A | 1/1995 | Herron et al. |
| 5,436,161 | A | 7/1995 | Bergstrom et al. |
| 5,492,840 | A * | 2/1996 | Malmqvist et al. ......... 436/518 |
| 5,512,492 | A | 4/1996 | Herron et al. |
| 5,552,272 | A | 9/1996 | Bogart |
| 5,580,794 | A | 12/1996 | Allen |
| 5,637,469 | A * | 6/1997 | Wilding et al. ............ 435/7.21 |
| 5,677,196 | A | 10/1997 | Herron et al. |
| 5,814,565 | A | 9/1998 | Reichert et al. |
| 5,832,165 | A | 11/1998 | Reichert et al. |
| 5,846,842 | A | 12/1998 | Herron et al. |
| 5,919,712 | A | 7/1999 | Herron et al. |
| 5,961,924 | A | 10/1999 | Reichert et al. |
| 5,965,456 | A * | 10/1999 | Malmqvist et al. ......... 436/514 |
| D426,783 | S | 6/2000 | Christensen et al. |
| 6,108,463 | A | 8/2000 | Herron et al. |
| 6,316,274 | B1 * | 11/2001 | Herron et al. .............. 436/518 |

FOREIGN PATENT DOCUMENTS

| | | |
|---|---|---|
| EP | 0 517 516 A1 | 12/1992 |
| EP | 0 519 623 A2 | 12/1992 |
| GB | 2220083 | 12/1989 |
| MX | 943673 | 10/1995 |
| WO | WO 81/00912 | 4/1981 |
| WO | WO 89/09408 | 10/1989 |
| WO | 9001166 | 2/1990 |
| WO | 9006503 | 6/1990 |
| WO | 9 113 339 | 9/1991 |
| WO | 9115751 | 10/1991 |
| WO | 9209892 | 6/1992 |
| WO | 9 216 838 | 10/1992 |
| WO | WO 92/16838 | 10/1992 |

OTHER PUBLICATIONS

Ciana, Leopoldo Della, "Electrochemiluminescence Immunosensors And DNA Probes For Clinical Diagnostics", Abstract, p. 19.

Fitch, R., "Polymer Colloids: A Comprehensive Introduction", *Academic Press, Inc.*, 10 pages, 1997.

Harmer, "Guided–Wave Chemical Sensors", *Electrochem. Soc.* 87–9 (Proc. Synp. Chem. Sens.), pp. 409–427, 1987.

Harrick et al., "Multiple Internal Reflection Fluorescence Spectrometry", *Analytical Chemistry*, vol. 45, No. 4, pp. 687–691, Apr. 1973.

Herron, "Fluorescent immunosensors using planar waveguides", *SPIE*, vol. 1885, Proceedings of Advances in Fluorescence Sensing Technology, pp. 28–39, 1993.

Huang, Shao–Chie, "PEG derivatives as tethers for site–directed immobilization of oxidized antibody", title page, abstract (pp. iv–v), and pp. 35–39.

Huang, Shao–Chie, "PEG Derivatives As Tethers For Site–Directed Immobilization Of Oxidiz d Antibody", Master's Thesis, Nov. 1991.

Ives, Jeffrey T., "Optical waveguide sensors: characterization of evanescent and scatter excitation," Ph.D. dissertation submitted to Dept. of Bioengineering, University of Utah, Jun. 1990.

*J. Chromatography 604*: 63–71, Caldwell, Li, Li and Dalgleish, "Adsorption behavior of milk proteins of polystrene Itex", Elsevier Science Publishers, 1992.

Lee, "Protein–resistant surfaces prepared by PEO–containing block copolymer surfactants", *Journal of Biomedical Materials Research*, pp. 351–368, 1989.

Lakowicz, Joseph R., "Fluorescence Lifetime–Based Sensing And Imaging", Abstract, p. 5.

Leiner, M.J.P., "Optical Sensors For In Vitro Blood Gas Analysis", Abstract.

Ligler et al., "Evanescent Wave Optical Fibre Sensors", Abstract, p. 75.

Liu, Benjamin L., "Clinical Requirements For Optical Immunosensors", Abstract, p. 13.

Masuda, Kenji, "Study Of The Sensitivity Of Evanescent Wave Immunoassay", Abstract, p. 11.

*Multiple Internal Reflection Fluorscence Spectrometry*, Harrick, N.J., and Loeb, George I., Analytical Chemistry, vol. 45, No. 4, Apr. 1973, pp. 687–691.

O'Keeffe et al., "Development Of A LED Based Phase Fluorimetric Oxygen Sensor Using Evanescent Wave Excitation Of A Sol–Gel Immobilized Dye", Abstract, p. 149.

O'Neill et al., "Use Of An Optical Biosensor To Measure Prostate Specific Antigen In Whole Blood", Abstract, p. 20.

*Particle Size Distribution II*, Li, J., Caldwell, K.D., and Tan, J.S., Chapter 16, "Size analysis of a block copolymer-coated polystyrene latex", pub. American Chemical Societym 1991.

Robinson, Grenville, "The Commerical Development Of Planar Optical Biosensors", Abstract.

Sacco et al., "Fibre–Fluorescence Immunosensors Based On Evanescent Wave Detection", Abstract, p. 52.

Slovacek et al., "Application Of A Plastic Evanescent Wave Sensor To Immunological Measurements Of CKMB", Abstract, p. 16.

van Erp et al., "Affinity of monoclonal antibodies", *J. Immunol. Methods*, 140:235–241, 1991.

* cited by examiner

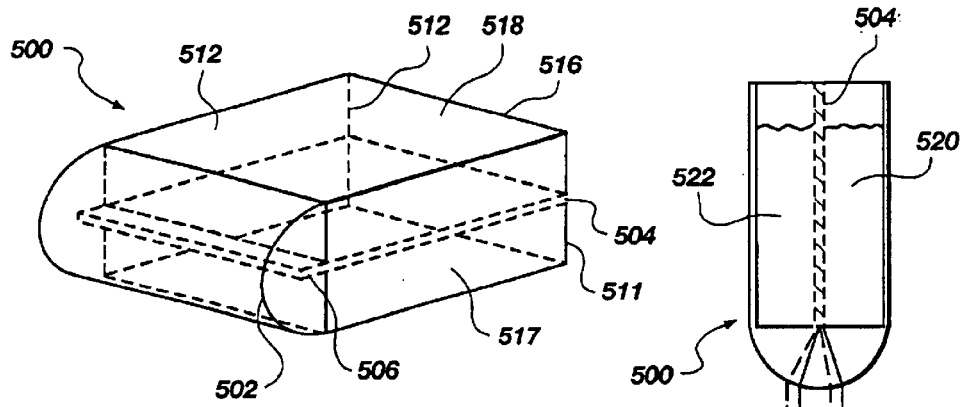
Fig. 5A
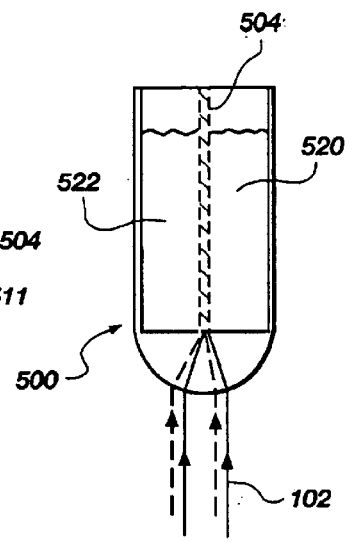
FROM LIGHT SOURCE
Fig. 5C
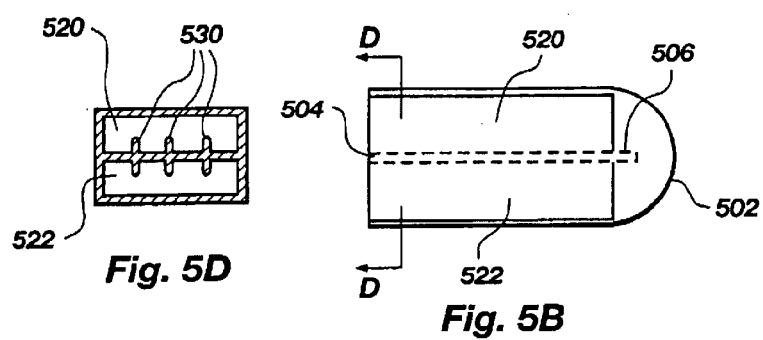
Fig. 5D
Fig. 5B
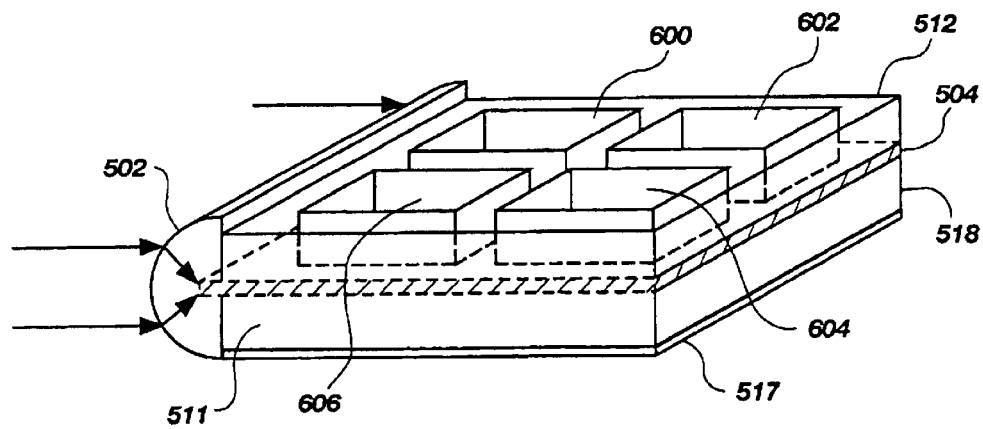
Fig. 6

APPARATUS AND METHODS FOR MULTI-ANALYTE HOMOGENEOUS FLUORO-IMMUNOASSAYS

RELATED APPLICATIONS

This application is a continuation of application Ser. No. 09/516,307 filed on Mar. 1, 2000, now U.S. Pat. No. 6,316,274, issued Nov. 13, 2001, which is a divisional of application Ser. No. 08/979,582 filed on Nov. 26, 1997, abandoned, which is a continuation-in-part of U.S. patent application Ser. No. 08/748,687, filed on Nov. 13, 1996, now U.S. Pat. No. 5,919,712, issued Jul. 6, 1999, which is a divisional of U.S. patent application Ser. No. 08/263,522, filed Jun. 22, 1994, now U.S. Pat. No. 5,677,196, issued Oct. 14, 1997, which is a continuation-in-part of application Ser. No. 08/110,169, filed Aug. 20, 1993, now U.S. Pat. No. 5,516,703, issued May 14, 19996, and application Ser. No. 08/071,579, filed Jun. 2, 1993, now abandoned, which is a continuation-in-part of application Ser. No. 08/064,608, filed May 18, 1993, now U.S. Pat. No. 5,512,492, issued Apr. 30, 1996.

TECHNICAL FIELD

This application relates to the art of analyzing samples for particular substances by means of fluorescent binding assays and, more particularly, to apparatus, compositions and methods for such assays employing evanescent light.

BACKGROUND

Biosensor apparatus based on optical detection of analytes by fluorescence of tracer molecules have attracted increasing attention in recent years. Such apparatus are useful for both diagnostic and research purposes. In particular, biosensors for a solid-phase fluoroimmunoassay, in which an antibody or antibody fragment specific to the desired analyte is immobilized on a substrate and binding of the analyte to the antibody results either directly or indirectly (for example, by means of a labeled tracer) in a fluorescence signal, are becoming an important class of optical biosensor.

In most solid-phase fluoroimmunoassays, to achieve adequate sensitivity, a "wash" step is required to remove unbound tracer before measuring the fluorescence. This problem is particularly true for detection of analytes present at concentrations below nanomolar, as is the case for many analytes of interest in body fluids including blood, serum and urine. However, the wash step is tedious, and care on the part of the technician is required to produce repeatable and accurate results. Accordingly, it is highly desirable to provide a fluoroimmunoassay system in which sensitivity to analyte concentrations of $10^{-10}$ to $10^{-13}$ molar or below is achieved without a wash step.

An optical technique known as total internal reflection (abbreviated TIR) provides one approach to such a system. Evanescent light is light produced when a light beam traveling in a waveguide is totally internally reflected at the interface between the waveguide and a surrounding medium having a lower refractive index. A portion of the electromagnetic field of the internally reflected light penetrates into the surrounding medium and constitutes the evanescent light field. The intensity of evanescent light drops off exponentially with distance from the waveguide surface. In a fluoroimmunoassay, evanescent light can be used to selectively excite tracer molecules directly or indirectly bound to an immobilized binding agent, while tracer molecules free in solution beyond the evanescent penetration distance are not excited and thus do not contribute "background" fluorescence. The use of evanescent field properties for fluorescence measurements is sometimes referred to as evanescent sensing. For a glass or a similar silica-based material, or an optical plastic such as polystyrene, with the surrounding medium being an aqueous solution, the region of effective excitation by evanescent light generally extends about 1000 to 2000 Å (angstroms) from the waveguide surface. This depth is sufficient to excite most of the tracer molecules bound to the capture molecules (antibodies, receptor molecules, and the like, or fragments thereof) on the waveguide surface, without exciting the bulk of the tracer molecules that remain free in solution. The fluorescence thus resulting reflects the amount of tracer bound to the immobilized capture molecules, and in turn the amount of analyte present.

The tracer fluorescent light will, conversely, also evanescently penetrate back into the waveguide and be propagated therein. The maximum solution depth for efficient evanescent collection by the waveguide approximates the depth of the region of evanescent penetration into the solution, and thus the waveguide-penetrating portion of the tracer fluorescence can also be used to selectively measure fluorescence from tracer bound to the waveguide surface.

U.S. Pat. No. RE 33,064 to Carter, U.S. Pat. No. 5,081,012 to Flanagan et al., U.S. Pat. No. 4,880,752 to Keck, U.S. Pat. No. 5,166,515 to Attridge, and U.S. Pat. No. 5,156,976 to Slovacek and Love, and EP publication Nos. 0 517 516 and 0 519 623, both by Slovacek et al., all disclose apparatus for fluoroimmunoassays utilizing evanescent sensing principles.

Desirably, an immunofluorescent biosensor should be capable of detecting analyte molecules at concentrations of $10^{-12}$ M (molar) or below. To date, most reports of evanescent-type biosensors indicate that, at best, concentrations of $10^{-11}$ M could be detected.

It is further desirable for speed and convenience in "routine" testing, for example, testing of blood bank samples for viral antibodies, to have an evanescent immunofluorescent biosensor which is disposable and which provides multi-sample measurement capability. Multi-sample capability would allow a test sample and a control sample (such as a blank, a positive control, or, for a competition-type assay, a sample preloaded with tracer molecules) to be simultaneously illuminated and measured. Simultaneous multi-sample capability would also speed up the process of analyzing multiple samples and would reduce the effects of variation in the level of exciting light which are known to occur with typical light sources. However, in a typical prior art evanescent light device such as that of Block et al., U.S. Pat. No. 4,909,990 issued Mar. 20, 1990, the waveguide is a fiber optic rod whose shape makes it difficult to build a multi-well biosensor.

Another factor which affects the attainable sensitivity relates to the intensity of excitation light emitted from the waveguide. The intensity of fluorescence emitted by tracer molecules is in part dependent on the intensity of exciting light (which is the evanescent field). Therefore, increased evanescent light intensity should provide increased fluorescence which in turn would improve the detection sensitivity. The level of evanescent light is in turn dependent on the intensity of the light beam propagating in the waveguide, and this can be increased by decreasing the cross-sectional area of the waveguide.

Previous methods of immobilizing antibodies to optical substrates in evanescent biosensors also present some problems causing reduction in sensitivity. Many such methods utilize the ε-amino groups of lysine residues in the protein. This approach has at least two significant disadvantages due to the fact that most proteins have multiple lysine residues. First, the presence of multiple potential coupling sites (multiple lysine residues) results in multiple random orientations of antibodies on the substrate surface. If the substrate-coupled lysine residue is near the N-terminal of the antibody molecule, the antibody's antigen binding site (which is near the N-terminal) may be effectively unavailable for binding of the analyte.

Second, if multiple lysines on the same antibody molecule are coupled to the substrate, the molecule may be subjected to conformational strains which distort the antigen binding site and alter its binding efficiency. For capture molecules immobilized by typical prior methods, generally only 20% or less of the binding sites are functional for analyte binding. Thus, it is desirable to have a site-specific method for coupling of the antibodies or other proteins, so that the capture molecules will be uniformly oriented and available for analyte binding.

Another problem relates to the levels of nonspecific binding to the antibody-coated surface of the optical substrate. These levels are often sufficiently high to make detection of analyte at concentrations below about $10^{-10}$ M very difficult. Nonspecific binding can be reduced by including a wash step after the sample is incubated with the coated substrate to remove unbound tracer molecules. However, as discussed above, a wash step is undesirable. Second, nonspecific binding can be a serious problem unless the surface is "passivated" with a masking agent such as bovine serum albumin or with a thin coating of hydrophilic polymer such as poly(ethylene glycol) or poly(methacrylate). Without such passivation (which introduces yet another step into the procedure), nonspecific binding can be 50% or more of the specific binding. Even with passivated surfaces, nonspecific binding can be sufficient to reduce detection sensitivity and reproducibility.

Thus, a need remains for an evanescent biosensor system which provides the desired sensitivity in a homogeneous assay (homogeneous being defined for purposes of this application as meaning an assay that does not require a wash step). A need further remains for such an apparatus with improved sensitivity for detection of analytes at picomolar concentrations and below. A need also remains for an immunofluorescent assay and biosensor with properties of low nonspecific binding and having uniformly oriented capture molecules. A need also remains for such a biosensor and assay system which are inexpensive and readily used by non-skilled persons.

SUMMARY OF THE INVENTION

The invention comprises a system including both apparatus and methods for a homogeneous immunofluorescence assay based on evanescent light principles and capable of detecting one or more analytes at concentrations less than pico-molar. The overall configuration of the apparatus is such that fluorescence-emitting tracer molecules bound to a waveguide surface are excited by an evanescent field penetrating into the adjacent solution from a light beam propagated within the waveguide, the propagated beam being introduced at an end or edge of the waveguide. The emitted fluorescence is then directly collected from the zone of evanescent penetration, e.g., not from an edge or end of the waveguide.

The apparatus includes a biosensor comprising a planar waveguide having a receiving region on its edge for receiving light to be internally propagated. A semicylindrical lens is integrally adapted to the waveguide edge adjacent the receiving region, and at least one of the waveguide surfaces has a plurality of capture molecules immobilized thereon. The capture molecules may include a plurality of species, each configured to specifically bind a different analyte, and different species may be localized in different and mutually exclusive regions on the waveguide surface. In a highly preferred embodiment, the semicylindrical lens and the waveguide are integrally molded of an optical plastic, and the lens is oriented to aim the beam at a selected angle to the plane of the waveguide, the selected angle being less than the critical angle of reflection at the waveguide-liquid interface. The waveguide also may have a serrated portion forming the portion of the edge opposite the receiving region.

The apparatus further includes a light source configured and disposed to deliver a sheet beam of light into the waveguide through a receiving region on the edge and detection means disposed for direct collection of fluorescence from the evanescent zone, direct collection being defined as not requiring propagation of the fluorescent light in the waveguide. The detection means is desirably an imaging detector configured to simultaneously separately collect a plurality of fluorescence signals, each originating from a different region on the waveguide surface. The imaging detector includes a plurality of photodetection elements spaced from each other in the displaced parallel plane and lens means positioned to focus each of the fluorescence signals onto a respective one of the photodetection elements.

The invention further encompasses methods for site-specifically immobilizing the capture molecules to the waveguide surface, methods for coating silica and polystyrene waveguide surfaces to reduce nonspecific binding, methods of patterning a waveguide surface with patches of different capture molecule species using photo-affinity crosslinking agents, and waveguides prepared by any of these methods singly or in combination. The method for patterning the waveguide with patches of different capture molecules involves localized irradiation of one or more regions of the waveguide surface in the presence of a photo-affinity crosslinking agent. In a highly preferred method, the waveguide surface is coated with a coating agent which inhibits nonspecific protein binding to less than 5%–10%, and preferably as low as 1% to 2%, of nonspecific binding. Also preferably, the capture molecules are coupled to the waveguide in a site-specific manner. For site-specific coupling, Fab' fragments are preferred as these are easily prepared with thiol sites, the thiol sites being highly suitable for the surface coupling chemistry. The preferred method of photo-activated crosslinking agent also utilizes thiol sites on the capture molecules. The site-specific coupling chemistry provides waveguide surfaces having 50% to 70% of the capture molecules with analyte binding sites readily available for binding.

BRIEF DESCRIPTION OF THE DRAWINGS

FIG. 5A is an elevational view of an alternate embodiment of a multi-channel biosensor;

FIG. 5B is a side view of the biosensor of FIG. 5A;

FIG. 5C is a side view of the biosensor of FIG. 5A in a vertical orientation with a sample solution therein;

FIG. 5D is a cross-sectional view of the biosensor taken along line D—D in FIG. 5B;

FIG. 6 is an elevational view of an alternate embodiment of a multiwell biosensor;

DETAILED DESCRIPTION OF THE ILLUSTRATED EMBODIMENTS

Figure 1:
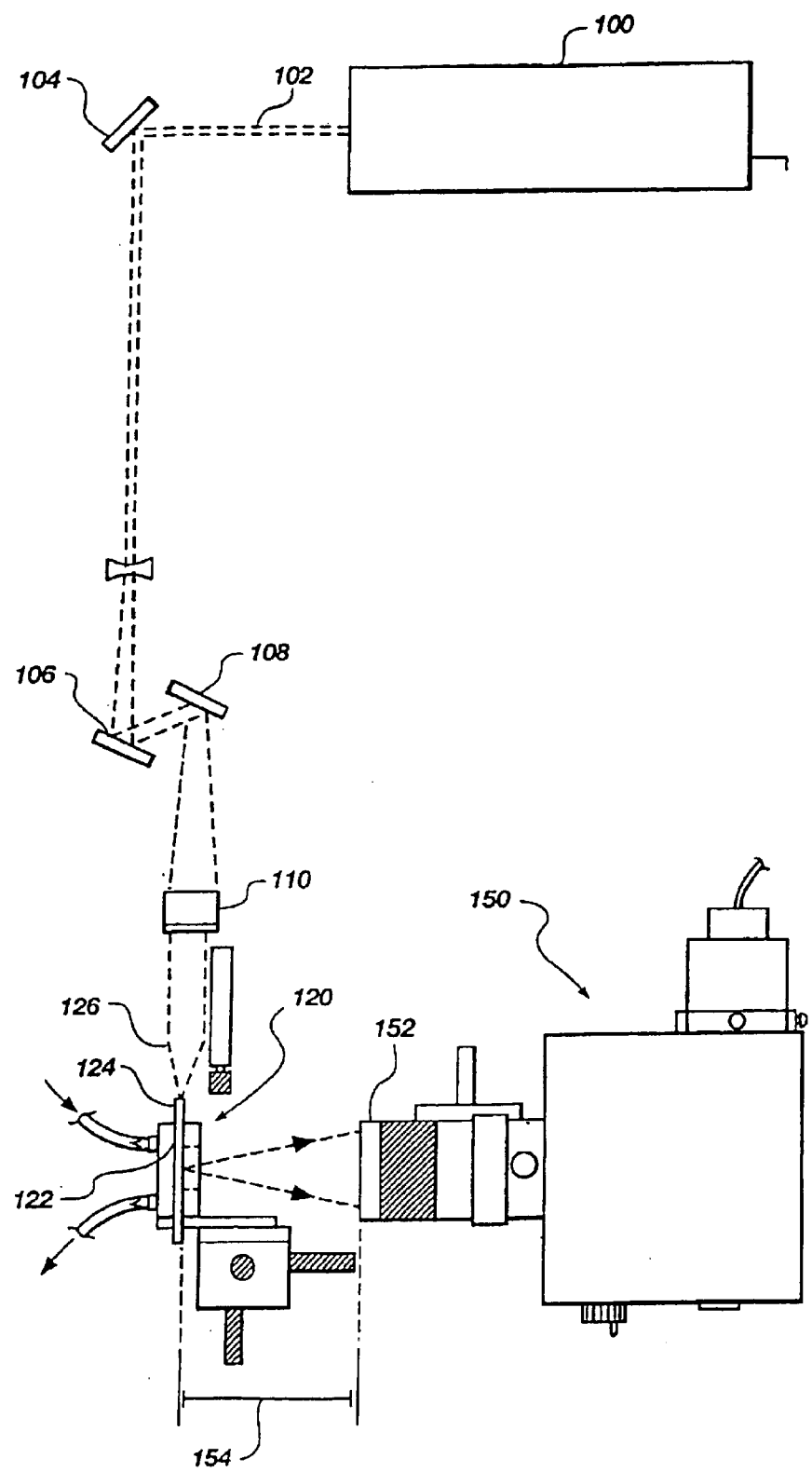
FIG. 1 is a schematic diagram of a fluorescent immunoassay apparatus of the invention.

A light source 100 provides a light beam 102 which is directed by means of mirrors 104, 106, 108 to an optical biosensor indicated generally at 120 (FIG. 1). In the working embodiment, light source 100 is an argon laser capable of emitting light at wavelengths of between about 488 and 514.5 nanometers (abbreviated nm). In an alternate embodiment, a laser diode emitting at wavelengths of 600 to about 700 nm can be used as light source 100. Depending on the requirements of the fluorescent tracer, light source 100 may also be embodied as any other laser or other high-intensity light source emitting a sufficient amount of light at an appropriate wavelength to excite the selected tracer.

The embodiment of FIG. 1 further includes a 45° angle mirror 10 which is positioned for making beam 102 a vertical beam prior to focusing the beam onto the biosensor. It will be understood by those skilled that the number and arrangement of mirrors 104, 106, 108, 110 may be varied as necessary to accommodate various space limitations, with the sole requirement being that a sufficient amount of light be directed to biosensor 120.

Figure 2:
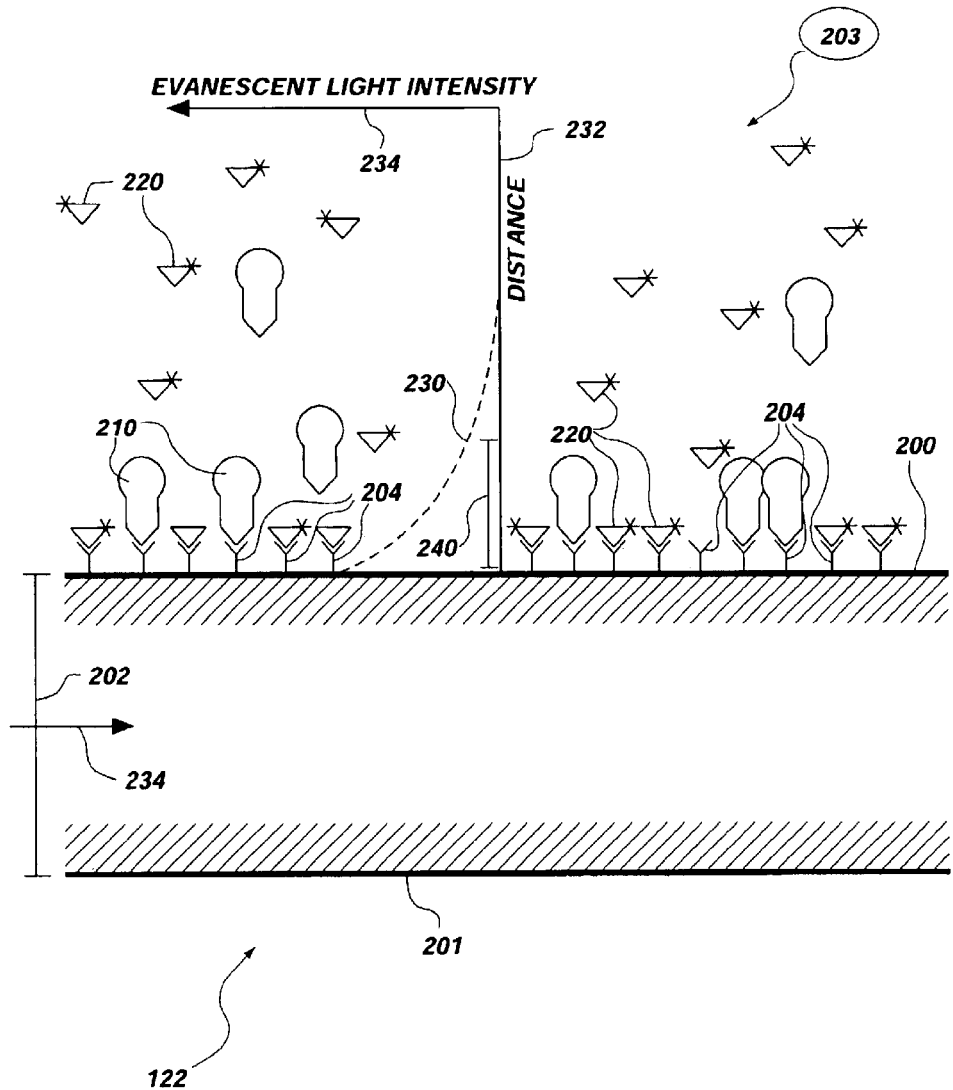
FIG. 2 is a side view of a portion of the waveguide and the biochemical components of a competition assay according to the invention.

Biosensor 120 has an optical substrate 122 with one end 124 positioned to receive light from beam 102. A focusing lens 126 is positioned between 45° angle mirror 110 and end 124 of optical substrate 122 for focusing light from beam 102 onto end 124. Focusing lens 126 is here shown mounted on an X-Y translation unit so that its position may be adjusted for best focusing. In contrast to the rod-shaped fiber optic waveguides typically found in immunofluorescent assay devices, in the present invention, optical substrate 122 is of generally planar shape having two planar surfaces spaced by a width, as shown in FIG. 2. Optical substrate 122 may, for example, be a square or rectangular glass microscope slide or coverslip, or the like. Materials for optical substrate 122 include glass, high-lead glass, quartz, optical plastic, and the like as are well-known in the art.

Referring again to FIG. 1, light detection means, indicated generally at 150, are positioned to detect fluorescent light emitted from biosensor 120. The emitted light is reflective of the concentration of a selected analyte in a sample, as is better described subsequently in reference to FIGS. 2 and 7–10. Light detection means 150 includes a collection lens 152 positioned to collect the emitted fluorescence from a plane parallel to and displaced from the surface of optical substrate 122.

The distance 154 between collection lens 152 and optical substrate 122 is selected as known to those skilled to maximize the collection of light emitted from the region of evanescent light penetration. The light collected by collection lens 152 is then sent to detection means 150, which responds by outputting signals reflective of the level of collected fluorescent light.

Detection means 150 may be any type of photodetector useful to detect light in the wavelength region spanning the wavelength range of the emitted fluorescence, as known in the art. However, in a preferred embodiment for simultaneous multi-analyte assays, detection means 150 is an imaging-type detector providing direct imaging of each of the fluorescent signal(s) originating in the evanescent zone 240, which is also referred to herein as an "excitation zone," as fluorescent molecules within the evanescent zone 24 are excited into a fluorescent state. In the apparatus of FIG. 1, detection means 150 is a CCD (charge-coupled device) detector which produces a signal like that depicted in FIG. 4C. Such imaging signal collection provides simultaneous measurement of multiple samples in a much simpler way than a system in which a separate optical element is needed to read each well or patch. The present imaging detection system also provides for collection of emitted fluorescence directly from the evanescent zone 240 (FIG. 2), rather than via evanescent penetration and propagation of the fluorescence in the waveguide.

Alternatively, detection means 150 may be a photomultiplier, a semiconductor photodiode, or an array of such detectors. In embodiments other than a CCD, an array is generally preferable to a single detector for some purposes. With an array of small detectors, the user can determine that the peak fluorescence is being detected and is not inadvertently missed due to misalignment of the collection and detection optics. Optionally, a grating spectrograph is coupled to the CCD or other detection means to provide spectral analysis of the detected light. In that case, means are also provided to integrate the signal function around each peak to determine the total collected fluorescence from a sample. Alternatively, in an embodiment for use in a setting such as in a testing laboratory, and for which all the parameters of the assay have been standardized, the spectrograph may be replaced by a filter which passes only wavelengths in the region of tracer fluorescence.

Figures 14A, 14B:
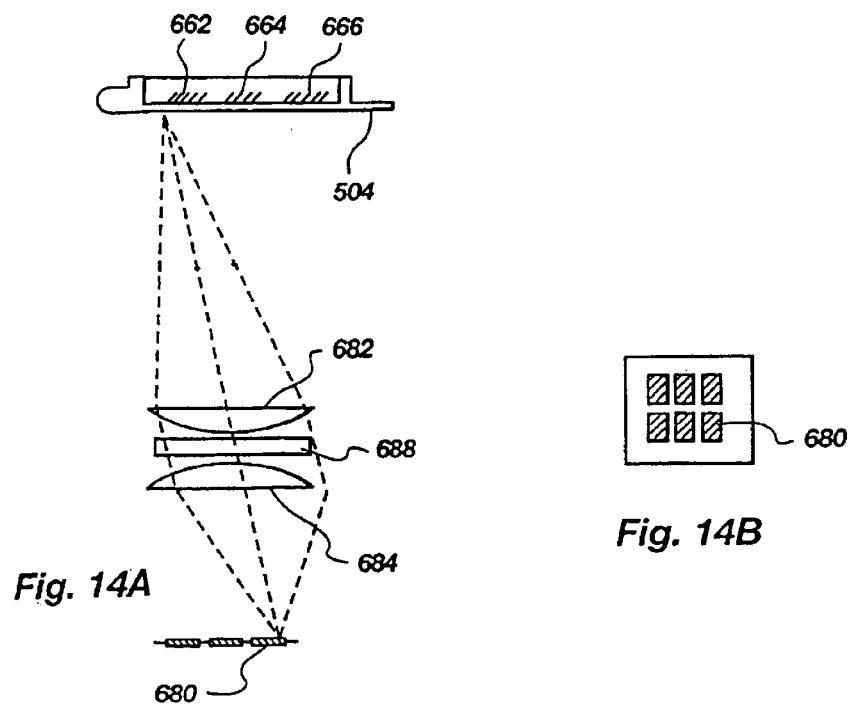
FIGS. 14A and 14B are a side view diagram of an improved imaging photo-detection system and a top view of a photodiode array for use in the system, respectively.

FIGS. 14A and 14B depict an alternate and presently preferred embodiment of an imaging detection system, which may be substituted for the CCD imaging detector of FIG. 1. In this embodiment, an array of photodiodes 680 is arranged with respect to a detection lens means such that light from a given patch located on waveguide 504 is focused onto a corresponding photodiode (FIG. 14A). In this embodiment, the detection lens means comprises a pair of opposingly oriented lenses 682, 684. The apparatus having the imaging detection system of FIGS. 14A–B is substantially less expensive to make than one having a CCD detector. The patches 662, 664, 666 should be spaced appropriately to correspond to the size and spacing of the photodiodes, the focal length and magnification of the lens, and the distance between the waveguide 504 surface, the detection lens or lenses, and the photodiode array, as generally understood in the art of optics.

Desirably, one or more filters 688 are positioned adjacent the detection lens, and preferably between two detection lenses 682, 684 as shown in FIG. 14A. This arrangement provides for effective filtering of scattered excitation light and other stray light prior to impingement of the signal light on the photodiodes. The filter(s) can be of either bandpass or long-pass type, and the wavelength region to be passed will depend upon the wavelengths of the excitation light and the fluorescent light of the tracer molecule. For example, with laser diode excitation at 635 nm of the cyanine dye CY5 which has peak fluorescence at 670 nm, filters passing light longer than about 650 nm in wavelength are useful. In a presently preferred embodiment, a bandpass filter centered at 670 nm with a 40 nm line-width is used.

Figure 3C:
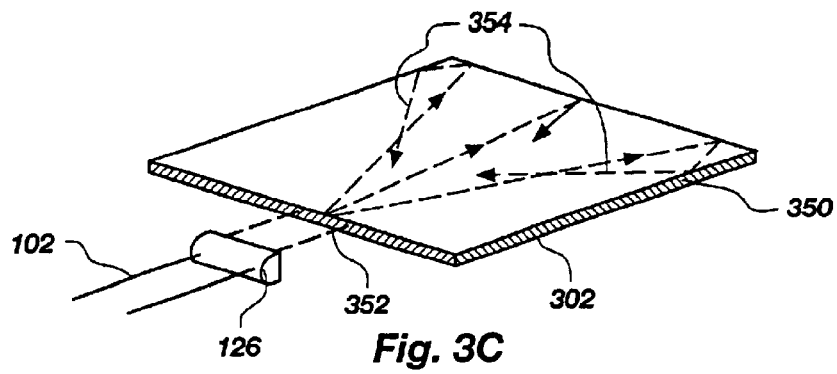
FIG. 3C shows the waveguide in isolation as it could be arranged with respect to a cylindrical lens and incoming and reflected light waves.
Figure 11A:
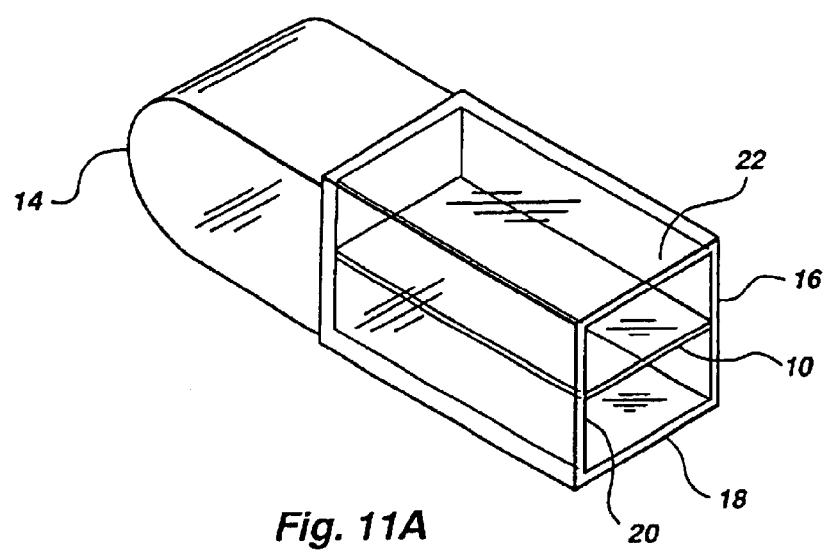
FIG. 11A is an elevational view of another embodiment of a biosensor.

For focusing light beam 102 onto the end of the planar substrate waveguide, it is preferred to replace the typical spherical lens with a lens of semicylindrical shape, as better seen in FIGS. 3C, 5A, and 11A. For purposes of this application, "semicylindrical" is defined to include both a transection of a right circular cylinder along a plane parallel to the vertical axis of the cylinder and a transection of a right cylinder having bases of an elliptical shape. Thus, the lens shape may be similar to the type known as aspherical. A hyperboloid cross-section may also be suitable. The shape and dimensions of the curved surface of the lens should, however, be longitudinally uniform along the region used for focusing of the light beam.

As is better seen in FIG. 2, optical substrate 122 is embodied as a planar waveguide having at least one planar surface 200 spaced from a second surface 201 by a width 202. At least planar surface 200 is disposed in contact with a sample solution 203. A plurality of capture molecules 204 are immobilized on surface 200. The sample solution contains a plurality of analyte molecules 210 of a selected analyte and a plurality of tracer molecules 220. The capture molecules are chosen or constructed to bind to a binding moiety present on each of the analyte molecules 210. The tracer molecule 220 is chosen or constructed to emit fluorescent light in response to stimulation by light of the appropriate wavelength. The level of fluorescence emitted by the tracer molecules 220 is a measure of the amount of analyte bound to the capture molecule and is thereby reflective of the concentration of analyte molecules 210 in the solution.

When light is being propagated in the optical substrate 122 and internally reflected at the surfaces 200, 201, an evanescent light field is produced having an intensity curve 230 which drops off with distance from the surface 200, as diagramed relative to a distance axis 232 and an intensity axis 234 (not to scale). An excitation zone 240 is the only region of the solution in which the evanescent light intensity is sufficient to excite a significant or detectable fraction of tracer molecules 220 (not to scale). Tracer molecules 220 outside zone 240 will contribute little or no induced fluorescence. Excitation zone 240 is typically between about 1000 and 2000 Å in depth.

Capture molecules 204 may be whole antibodies, antibody fragments such as Fab' fragments, whole antigenic molecules (haptens) or antigenic fragments, and oligopeptides which are antigenic and/or similar in three-dimensional conformation to an antibody-binding epitope. Capture molecules 204 may also be a receptor molecule of the kind usually found on a cell or organelle membrane and which has specificity for a desired analyte, or a portion thereof carrying the analyte-specific-binding property of the receptor.

In FIG. 2, a competition assay scheme is depicted (also termed a displacement assay). However, as will be apparent to the skilled person, alternate assay schemes such as sandwich assays may be performed with the present apparatus.

The capture molecules 204 may be immobilized on the surface 200 by any method known in the art. However, in the preferred embodiment, the capture molecules are immobilized in a site-specific manner. As used in this application, the term "site-specific" means that specific sites on the capture molecules are involved in the coupling to the waveguide, rather than random sites as with typical prior art methods. Examples I–III detail methods for site-specific immobilization of capture molecules to the surface of the optical substrate by means of a protein-resistant coating on the substrate.

As previously stated, the intensity of evanescent light drops off rapidly with distance from the waveguide surface. Thus, only tracer molecules which are within an effective excitation range 240 (not necessarily to scale) from the waveguide surface will be excited by the evanescent light to emit fluorescence. The range 240 is generally about 1000 to 2000 Å. This range is sufficient to ensure that essentially all tracer molecules 220 which are bound (directly or indirectly) to capture molecules 204 will be detected, while the bulk of the tracer molecules which remain free in solution are outside the effective excitation range.

In a working embodiment of the apparatus of FIG. 1, measurements of fluorescence are made by spectroscopy. For the examples involving rhodamine-tagged molecules, light source 100 is an argon ion laser (a LEXEL Model 95-2) at an emission wavelength of 514 nm. Fluorescence detection was done with a monochromator (SPEX Industries, Inc., Model 1680C) and a charge-coupled device (abbreviated CCD) (Photometrics Ltd. Series 200, or CH-250). Alternatively, light source 100 can be any light source emitting at the wavelength desired for excitation of selected fluorescent dyes. Also, once an assay procedure has been validated and standardized, it may not be necessary to measure the fluorescence spectrum or spatial distribution of fluorescence. The detection means may be simplified in accordance with the minimum requirements of the assay.

In an alternate and presently preferred embodiment, light source 100 is a laser diode emitting in the red wavelength region of 600–700 nm, available from Toshiba (part no. TOLD 9211). This laser diode provides about 5 milliwatts of power with a peak emission wavelength of about 670 mm. Laser diodes emitting at 630 nm are also available and can be used. For an embodiment using wavelength in this region, it is necessary to use dyes such as cyanine dyes, whose fluorescence can be stimulated by excitation with wavelengths in the red spectral region. An example of such a dye is CY5, available from Biological Detection Systems, Inc., Pittsburgh Pa. (catalog no. A25000). The CY5 dye can be conjugated to the desired tracer molecule by the manufacturer's instructions and/or with a kit available from BDS. A second dye, CY7, which is available from the same source, may also be suitable. The dyes and methods for conjugating are also characterized in the paper by Southwick, P. L., et al., titled "Cyanine Dye Labeling Reagents—Carboxymethylindo-cyanine Esers," *Cytometry* 11:418–430 (1990). The use of laser diodes as a light source permits the biosensor and waveguide to be formed of plastic, thereby reducing the manufacturing expense and facilitating the integral molding of the semicylindrical lens with the waveguide and reservoirs.

In the embodiment of FIG. 2, the immunoassay is a competition assay in which the tracer molecules 220 are constructed such that capture molecules 204 will bind analyte molecules 210 in place of tracer molecules 220. Higher concentrations of analyte molecules 210 will cause most of the tracer molecules 220 to be displaced into the surrounding solution from capture molecules 204, thus reducing the number of tracer molecules within excitation range 240 of the optical substrate 122. This reduced binding of tracer molecules in turn reduces the amount of fluorescence. In contrast, lower concentrations of analyte molecules 210 will allow tracer molecules 220 to bind to capture molecules 204, and thus to be held within the excitation range 240.

Figure 3B:
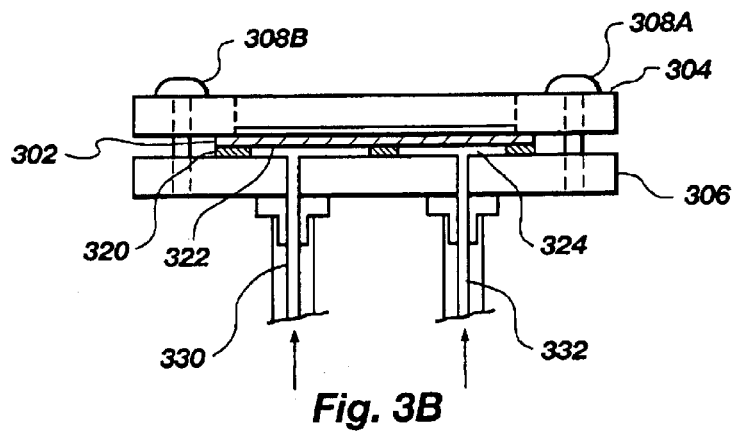
FIG. 3B is a side cross-section view of the flow biosensor taken along line B—B in FIG. 3A.
Figure 3A:
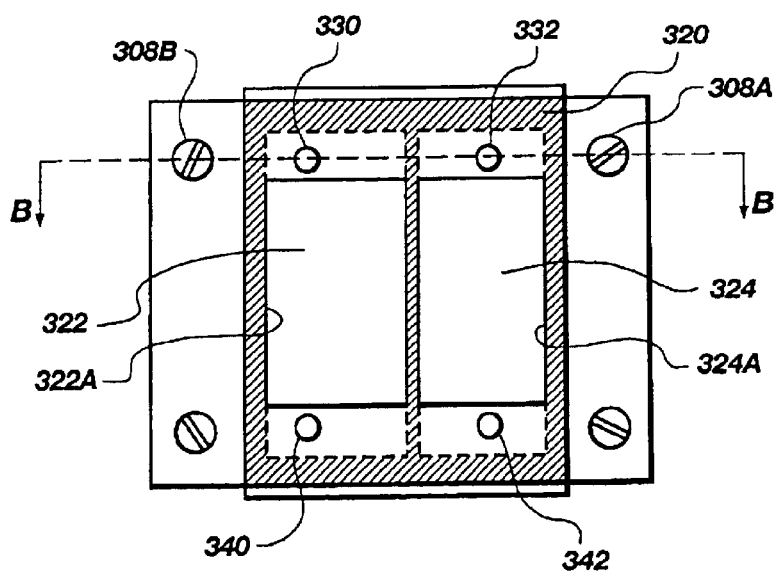
FIG. 3A is a top view of a flow biosensor of the apparatus of FIG. 1.

In the embodiment of FIG. 1, biosensor 120 is shown as a flow-through cell, shown in greater detail in FIGS. 3A–B. A planar waveguide 302 which may be, for example, a microscope slide or coverslip, is sandwiched between two plates 304, 306 which are held together by screw fittings 308A, 308B. A gasket 320 is seated between waveguide 302 and plate 306. Gasket 320 is configured with two internal openings which, when gasket 320 is securely sandwiched between plate 306 and waveguide 302, form reservoirs 322, 324. In reservoirs 322, 324, waveguide 302 constitutes one wall, plate 306 constitutes a second wall, and the inner edges 322A, 324A of the gasket 320 form the remaining walls. Although the reservoirs 322, 324 are here shown to be rectangular in shape, other shapes could be used. Also, instead of two reservoirs as depicted in FIG. 3A, the gasket could have either just one opening or more than two, creating corresponding numbers of individual reservoirs.

Gasket 320 is preferably made of a semirigid material having an index of refraction less than that of the waveguide material in the wavelength range of the exciting light. For the best results, it is believed that the index of refraction of the gasket material should be as low as possible compared to that of the waveguide. For a waveguide made of quartz or glass, the index of refraction would typically be from about 1.46 to 1.52, higher for high-lead glass. A transparent (non-pigmented) silicon rubber (siloxane polymer) with an index of refraction of 1.35–1.43 is a presently preferred material for gasket 320. TEFLON-type materials such as PTFE (polytetrafluoroethylene) or FEP (fluorinated ethylene propylene) have indices of refraction of around 10.34–1.35 and may also be suitable. However, because TEFLON surfaces tend to adsorb protein in a nonspecific manner, silicon rubber is generally preferred.

The lower plate 306 in FIG. 3B, has a pair of inlets 330, 332 and a pair of outlets 340, 342. These inlets and outlets are arranged so as to permit solutions to flow separately through the respective reservoirs 322, 324. Desirably, the lower plate 306 may be made from aluminum alloy.

FIG. 3C shows the waveguide 302 in isolation from the remaining parts of the biosensor. Lens 126 is shown receiving and focusing light beam 102 onto the waveguide 302. Desirably, the outer, surrounding edge 350 is coated with a reflective material, except for an uncoated region 352 at which the focused light from lens 126 enters the waveguide 302 (FIG. 3C). Arrows 354 indicate reflection from the coated edges. In FIG. 3C, only one lens and one uncoated region are shown; however, for two or more channels, more portions of edge 350 may be left uncoated to allow light to enter the waveguide 302 (see, for example, FIG. 4A).

The reflective coating reflects back into the waveguide light that would otherwise escape through the edge 350. The intensity of the evanescent field is thereby enhanced. Suitable reflective coating materials include aluminum, silver, or the like, as known in the art. Alternatively, in place of a coating, reflectors could be positioned about the edges to reflect escaping light back into the waveguide.

The design with at least two individual reservoirs has significant advantages over a single reservoir embodiment for instances in which it is desirable to measure the test sample fluorescence simultaneously with fluorescence from a control region on the same waveguide. For example, the level of nonspecific binding to the waveguide can be subtracted from the test sample fluorescence. Also, corrections can be made for measurement changes due to fluctuations in intensity of the exciting light. In a displacement assay, the "control" region could be the preloaded waveguide with no analyte present in the sample, or with a known amount of analyte. With three or more wells, fluorescence can be measured for both a no-analyte control and at least one known, calibration analyte sample in addition to the "unknown" or test sample.

Figure 4A:
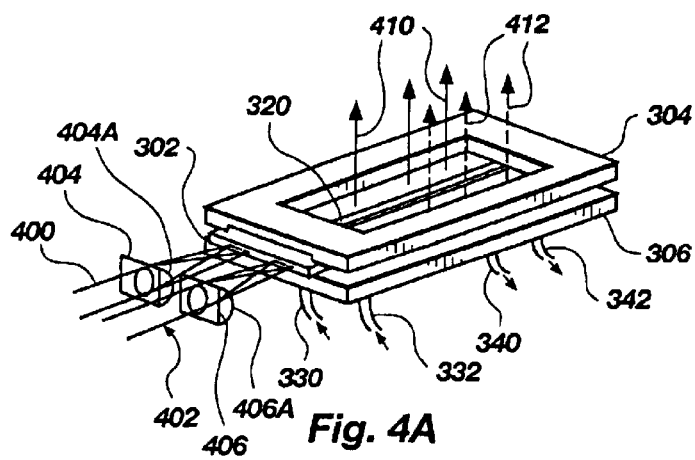
FIG. 4A is an elevational view of a two-channel flow biosensor of FIGS. 3A–3B with respect to exciting light beams and the collection of fluorescence.

FIG. 4A depicts the flow-through cell of FIGS. 3A–3B as it would be used for a waveguide excitation protocol. Here, the light beam is split into two equal components 400, 402 passing through respective focusing lenses 404, 406 to illuminate "channel 1" (CH.1) and "channel 2" (CH.2) in the waveguide 302. Solid arrows 410 indicate the direction from which fluorescence in CH.1 is collected, while dashed arrows 412 indicate the direction from which fluorescence in CH.2 is collected.

Figure 4B:
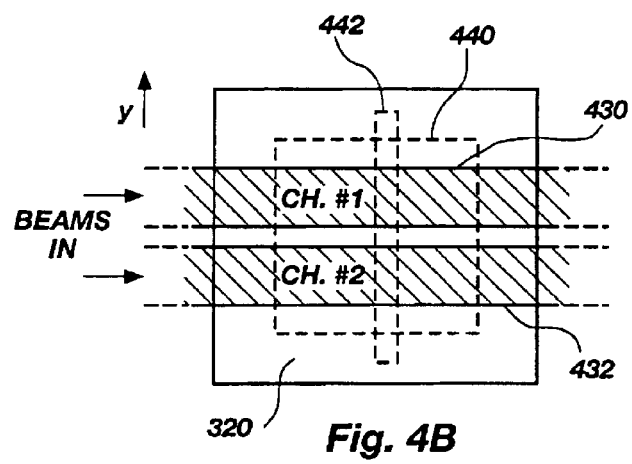
FIG. 4B is a schematic diagram of the two-channel biosensor indicating the arrangement of two components of the detection device, a CCD detector and the entrance spectrometer slit, with respect to the waveguide regions.
Figure 4C:
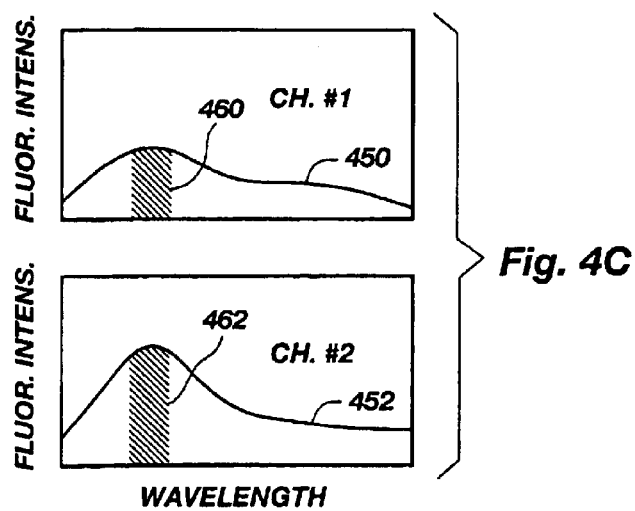
FIG. 4C is a diagram of fluorescence intensities as they might be detected from two channels of a biosensor arranged according to FIGS. 4A and 4B.

When the focusing lenses 404, 406 are properly aligned with respect to waveguide 302 and the light source, two illuminated strips 430, 432 (FIG. 4B) are visible which extend down the waveguide in the direction in which beam components 400, 402 are aligned. Box 440 represents an approximate outline of the detection region of the CCD array while box 442 represents an approximate outline of the spectrograph entrance slit. As previously described, one embodiment of a detection system comprises a spectrograph in combination with a CCD array. FIG. 4C depicts hypothetical expected results from such a detection system for simultaneous measurement of a "blank" or no-analyte sample in CH.2 and a test sample or "unknown" in CH.1. Curves 450, 452 respectively represent the fluorescence from CH.1 and CH.2. The fluorescent intensities of the blank and the sample would be compared by means of the values of the corresponding integrals of curves 450, 452 over the respective regions 460, 462. A calibration curve for a series of calibration samples of known analyte concentrations would typically be made and used to determine the concentration of an unknown sample, as known in the art.

Of further interest in FIG. 4A is the orientation of lenses 404, 406 with respect to waveguide 302. It will be seen that the curved edges 404A, 406A face towards waveguide 302, which is 180° from the orientation depicted in FIG. 3C. While the focusing lens can be oriented in either way, the arrangement of FIG. 4A is presently preferred for illumination of the waveguide with the flow-through cell.

FIGS. 5A–5D depict an alternate embodiment of a biosensor useful with the apparatus of FIG. 1. The biosensor indicated generally at 500 has an integrally mounted or formed focusing lens 502 and waveguide 504 arranged such that focusing lens 502 focuses light onto the forward end 506 of the waveguide 504. Focusing lens 502 is configured and positioned to focus a light beam 102 onto the forward end 506 of the waveguide 504 (FIGS. 5A, 5C). Sidewalls 511, 512, top and bottom walls 516, 517, and a removably sealing rear wall 518 enclose the space about the waveguide 504 to create reservoirs 520, 522.

The integral focusing lens 502 replaces focusing lens 126 in the apparatus of FIG. 1. In the working embodiment of FIGS. 5A–5D, the focusing lens 502 is molded as part of the biosensor 500 of an optical plastic such as polystyrene, polycarbonate or the like.

Biosensor 500 also includes reservoirs 520, 522, best seen in FIGS. 5B, 5C and 5D, in which sample solutions can be disposed. Optionally, for some applications it may be desirable to provide lengthwise ribs 530 (FIG. 5D) along waveguide 504 which can define separate regions of the waveguide surface.

FIG. 6 depicts an alternate multiwell biosensor similar to that of FIGS. 5A–5C, except that a series of discrete wells 600, 602, 604, 606 are formed on the waveguide 504. The embodiment of FIG. 6 would be used in a horizontal position, so that the wells 600, 602, 604, 606 need not be covered.

The biosensor including the lens may be formed by molding of a suitable optical plastic. A holder comprising the reservoir walls, the lens, and frame elements as needed may be pre-molded. A silica-surface waveguide is inserted subsequently with a refractive-index-matched adhesive to secure it in place and seal it as needed to create separate channels. Alternatively, the holder may be molded with a silica-surface waveguide in place, thereby eliminating the need for the adhesive.

In a presently preferred further embodiment, the waveguide is also formed of the optical plastic and is molded simultaneously with the lens and/or the reservoirs. The latter type of construction is not suitable for use with excitation wavelengths of 488 to 515 nm, because known optical plastics tend to emit fluorescence when excited in this (the blue and green) wavelength region. This fluorescence would appear as background fluorescence. However, an alternate embodiment of the apparatus using a light source emitting at wavelengths of 600 nm and above would accommodate a plastic waveguide. Molding the lens waveguide, or lens/waveguide/reservoir(s), as a single unit of plastic substantially reduces the cost of manufacturing and makes a disposable biosensor more feasible.

Figure 11B:
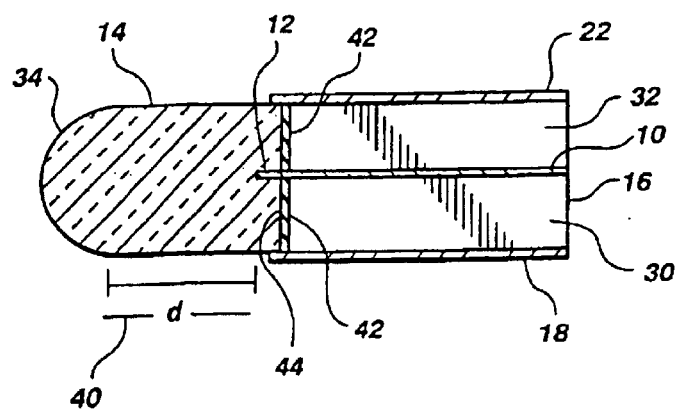
FIG. 11B is a side cross-section view of the biosensor embodiment of FIG. 11A.
Figure 11C:
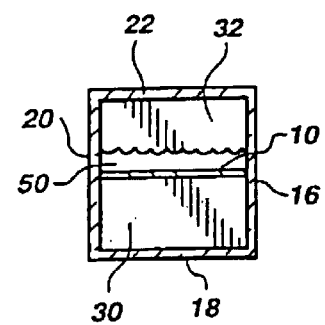
FIG. 11C is an end view of the biosensor embodiment of FIG. 11A.

FIGS. 11A–C show another embodiment of a biosensor similar to that depicted in FIGS. 3A–C. In FIG. 11A, waveguide 10 is a glass coverslip inserted in a sawcut groove 12 (FIG. 1B) in a solid, colorless plastic lens 14. Transparent walls 16, 18, 20, 22 are sealingly attached with index-matched adhesive to the lens 14 and about the edges of the waveguide 10 to form a pair of separate reservoirs 30, 32 (FIG. 11B).

In the embodiment of FIGS. 11A–C, the curved forward edge 34 of the lens 14 is spaced at a distance 40 from the forward end of the waveguide 10. Distance 40 is selected so as to match the focal length of the lens 14. A mask 42 made of a material that is opaque to visible light covers the rear edge 44 of lens 14. The embodiment of FIGS. 11A–C can be used in a vertical orientation as shown in FIG. 5C. Alternatively, the biosensor may be oriented with the waveguide 10 in a substantially horizontal position, so that only one side of the waveguide 10 is used. In such case, a cap which can sealingly close the open ends of the reservoirs must also be provided. An advantage of the horizontal orientation scheme is that only a thin layer 50 of sample solution is required (FIG. 11C). However, unless ribs along the waveguide 10 are provided, like ribs 530 in FIG. 5D, the biosensor of FIG. 11C in the horizontal orientation has only one effective sample channel.

While the curved edge 34 of lens 14 is shown as being substantially a semiright-cylinder in shape, other lens shapes are possible as described previously herein with respect to FIGS. 3A and 5C.

Figures 12A, 12B:
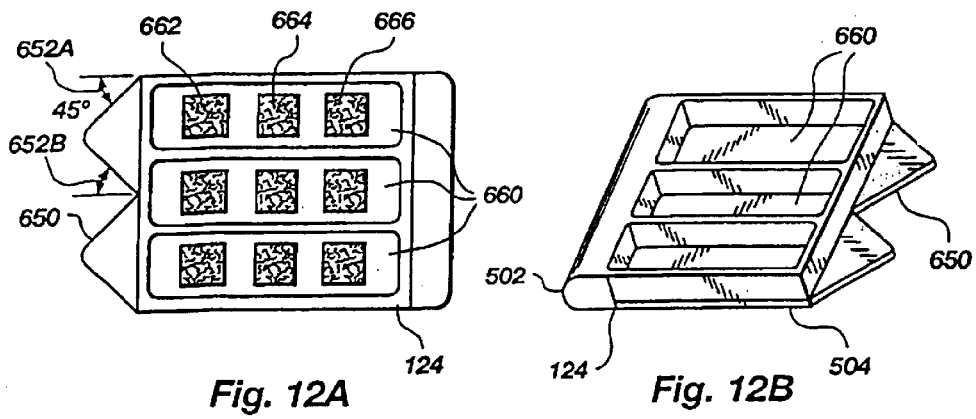
FIGS. 12A and 12B are a top view and an elevation view, respectively, of an alternate embodiment of an integrally molded biosensor.

In a further and highly preferred embodiment of the biosensor depicted in FIGS. 12A and 12B, the end of the planar waveguide which is distal to the receiving edge has a portion 650 that is serrated or toothed shape. The angles 652A, 652B must be less than the critical angle for total internal reflection at the waveguide-air interface (the critical angle for polystyrene/air is about 51°). Preferably, the sum of angles 652A, 652B should be 90°, so that the light is retro-reflected back along the longitudinal axis of the waveguide; still more preferably, angle 652A=652B=45°. An advantage of this shape is that it increases the level of internal reflection without a reflective coating on the edges, thus reducing manufacturing complexity and costs. The increased TIR enhances the evanescent field intensity and thus improves sensitivity of the assay. Also, the serrated end edge helps to equalize (make more uniform across the whole waveguide) the intensity of light within the waveguide. The entire waveguide portion of the biosensor should have an optical-quality surface, including the serrated end and the integral lens.

In a working embodiment, the waveguide is about 0.05 centimeters (cm) in thickness and the wells are about 0.08 to 0.1 cm in depth. The biosensor including the waveguide is about 2.5 cm wide and about 4.3 cm long.

The embodiment of FIGS. 12A and 12B also has a plurality of parallel wells 660, each extending along the longitudinal direction from the light-receiving end 124 of the waveguide. Notably, each well contains a plurality of patches 662, 664, 666, each comprising a different immobilized Fab' species. The elimination of separation walls between such different species, which would extend crosswise to the direction of light propagation in the waveguide, further increases the sensitivity of the assay. The increased sensitivity results from 1) avoiding leakage of waveguide light through the walls, and 2) avoiding scattering of the excitation light which may excite unbound tracer molecules outside the region of evanescent penetration, undesirably increasing background fluorescence.

Figure 13:
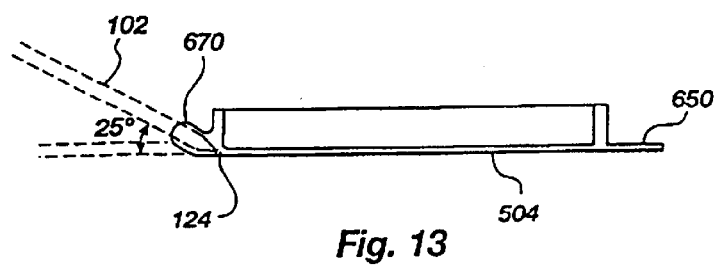
FIG. 13 is a side view of a molded biosensor with an alternate embodiment of the integral lens.

In another improvement, the sheet excitation beam is arranged to enter the receiving edge of the waveguide at an angle to the plane of the waveguide. FIG. 13 shows an angled integral lens 670 configured to accept such angled beam entry. For this purpose, the beam originating from the laser should be shaped to a sheet of a width approximating the width of the receiving region of the waveguide and of relatively narrow thickness (preferably no more than tenfold, and preferably one- to four-fold the waveguide thickness), using cylindrical and/or spherical lenses as known in the art.

The effect of so angling the beam entry is to increase the proportion of light exciting higher order modes that are propagated in the waveguide, thereby increasing the evanescent field intensity. The mean beam entry angle should be less than but near the critical angle of the waveguide/solution interface. The closer the beam entry angle is to this critical angle, the greater the increase in evanescent intensity. However, the beam entry angle should be sufficiently below the critical angle to avoid the possibility of exceeding the critical angle due to imperfections in the optical manufacture or otherwise inadvertently increasing the amount of input light escaping at the waveguide/solution interface, which would increase the amount of fluorescence from free tracer (the background level).

Figure 19:
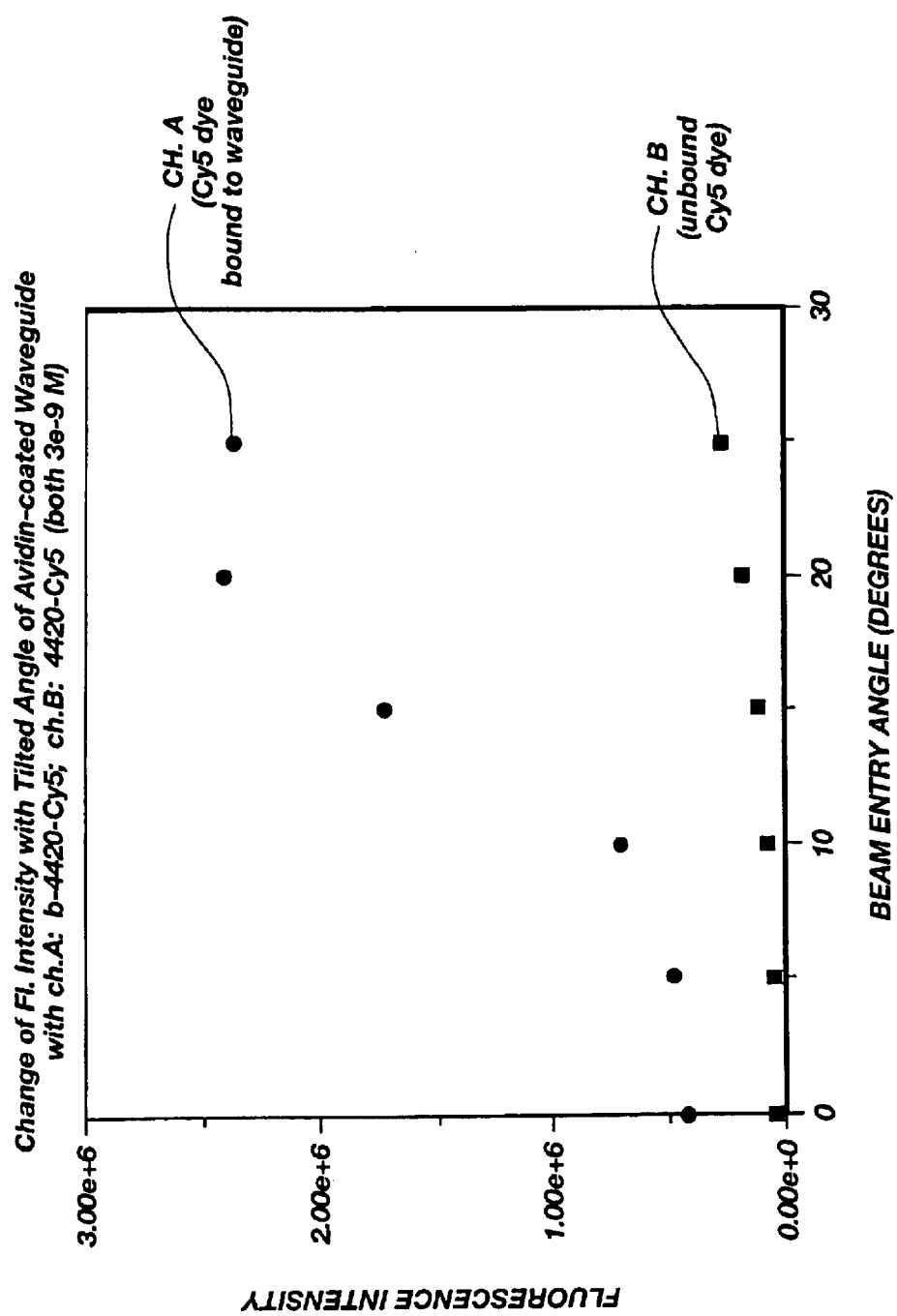
FIG. 19 is a chart comparing the intensity of detected fluorescence as a function of the angle of the input light lens to the waveguide surface.

FIG. 19 shows data for the fluorescence intensity of biotin-conjugated Cy5 dye bound to an avidin-coated silica waveguide (ch. A) as a function of beam entry angle, as compared to the "background" level of fluorescence from Cy5 dye free in solution (not conjugated to biotin and therefore not bound to the avidin-coated surface). The critical angle for TIR at the silica-aqueous solution boundary is about 26°. The data of FIG. 19 indicate that the signal-to-background ratio (ch.A+ch.B) for a beam entry angle of 20° to 25° is about 4-fold higher than for 0°. Thus, beam entry angles of one to about five degrees less than the critical angle are presently preferred for silica waveguides. For a polystyrene waveguide with an aqueous adjacent medium, the critical angle for TIR is about 33°, and a useful range of beam entry angles is from about 25° to about 32°, with the higher angles generally being preferable.

The use of an angled beam entry necessitates adjustment of the orientation of the center of radius of curvature of the semicylindrical lens with respect to the waveguide receiving end, as will be evident to a skilled person. In a molded integral biosensor, the integral lens/waveguide may be formed as shown in FIG. 13.

The following examples detail several methods for attaching the capture molecules to the waveguide surface in a site-specific manner. The general scheme for reducing the level of nonspecific binding is to coat the waveguide with a protein-resistant material and then immobilize the antibody to the coating. The scheme further includes derivatizing of the protein-resistant coating combined with site-specific modification of the antibody or other capture molecule to be immobilized, so as to provide site-specific attachment of the capture molecule to the coating.

Of the examples presented, the procedures of Examples I and II gave generally better results. At present, the avidin-biotin coupling method (Example II) is the most preferred. Using either coupling scheme, at least about 75% of the immobilized Fab' fragments were active, and the levels of nonspecific binding were typically no more than 1–2% of the specific binding. The modified PEG coating gave slightly higher levels of nonspecific binding, in the range of 5% to about 25%.

EXAMPLE I

Preparation of Waveguide Surface—Hydrogel

A silica surface was prepared with a hydrogel coating comprised of polymethacryloyl hydrazide (abbreviated PMahy). Fused silica slides of CO grade and thickness about 1 mm, available from ESCO, Inc., were suitable as waveguides (optical substrates).

To graft the PMahy to the silica, the surface was derivatized with aldehyde groups. The derivatization was accomplished by silanization with 3-aminopropyltriethoxy silane (abbreviated APS) to add an amino functional group, followed by reaction with glutaraldehyde to produce free aldehyde groups. The PMahy was then reacted with these aldehyde groups to form the hydrogel coating.

Antibodies could be coupled to this hydrogel in at least two ways. In one method, the carbohydrate groups in the Fc antibody region are oxidized to aldehydes by treatment with sodium metaperiodate. However, few antigen-binding fragments contain carbohydrate moieties useful for this purpose. Thus, a preferred method comprised modifying the pendant hydrazido groups of the hydrogel to a maleimido group by treatment with succinimidyl 4-(N-maleimido-methyl)cyclohexane-1-carboxylate (abbreviated SMCC; Pierce Chemicals). These maleimido groups can be reacted with the free thiol groups typically found in the C-terminal region of Fab' fragments, thereby coupling the Fab' fragments to the hydrogel.

Polymethacryloylchloride (abbreviated PMaCl) was prepared by radical polymerization of methacryloyl chloride (abbreviated MaCl) in dioxane under an inert atmosphere, as described in Jantas et al., *J. Polym. Sci., Part A. Polym. Chem.* 27:475–485 (1989).

A reaction mixture containing 21.1. mole % of MaCl, 78.1 mole % dioxane, and 0.8 mole % AIBN (azobisisobutyronitrile) was allowed to react for 24 hours at 60° C. with agitation. The PMaCl so produced remained in solution during the course of the reaction. The mixture was then diluted with twice the amount of dioxane used in the reaction and slowly added to an excess of hydrazine hydrate, to achieve a volumetric ratio of 2:5 for diluted PMaCl. The latter addition was carried out for about 30 minutes in an ice bath under a nitrogen atmosphere. The resulting mixture was then stirred for about an hour at room temperature. The product PMahy was purified by evaporation of dioxane and the remaining unreacted hydrazine hydrate, followed by washing in distilled water. The washed product was then dialyzed in a SpectraPor dialysis membrane having a molecular weight cut-off of 3,500 Dalton to remove unreacted monomer.

The polymer so prepared was shown to have a molecular weight of about 26,000 as measured by gel permeation chromatography for the hydrochloride form. The concentration of polymer in solution in the hydrochloride form was estimated to vary between about 5% and 8% (w/v). It has been found that the polymer can be stored in aqueous solution at 4° C. under a nitrogen atmosphere, for at least 5 months without undergoing a detrimental amount of spontaneous cross-linking.

Silica chips or glass or quartz microscope slides were cleaned with chromic acid, then treated with 5% APS/95% deionized water (v/v) for about fifteen minutes at room temperature. The APS-treated surfaces were rinsed with deionized water and absolute ethanol and incubated in a vacuum oven which had been flushed at least three times with nitrogen at 120° C. for 1 hour. The resulting silanized surfaces were then soaked in 2.5% glutaraldehyde (E.M. grade from Polysciences) in 0.1 M carbonate-bicarbonate buffer, pH 9.2, for two hours at room temperature.

Next, linear PMahy was reacted with the aldehyde groups on the treated chips to create a cross-linked polymer film with many unreacted hydrazido groups in the chains. This was done by dipping the treated chips in solutions of PMahy of between about 5% and 8% (w/v), pH 5.2, at a temperature between about room temperature and about 60° C., for a time sufficient to form a polymer film of a thickness of about 100 Å or less. The thickness of the hydrogel layer increases with time and temperature of incubation in the solution. It was found that optimal conditions for preparation of the film of 100 Å thickness or less comprised incubating in 5% (w/v) PMahy for 2 hours at room temperature (about 25° C.).

Next, the free hydrazido groups of the polymer film were modified by treatment with SMCC to provide reactive maleimido groups on the ends of the polymer side chains. This was done by immersing the PMahy-coated substrates in a solution of 0.19% (w/v) SMCC in dimethylformamide for about 1 hour at 25° C.

Following derivatization with SMCC, the hydrogel-coated surfaces were treated with a 1 mg/ml solution of Fab' fragments in phosphate buffer, pH 6.0, with 5 mM EDTA. The waveguide surface so prepared was shown to immobilize Fab' molecules at a surface density of about $1.4 \times 10-12$ moles/cm$^2$. Also the surface was able to immobilize Fab' fragments at their C-terminal thiol groups in a site-specific way. The thickness of the resulting polymer film was determined by ellipsometry to be about 100 Å, as was desired. This film thickness is much less than typical previous polymeric films, which have thicknesses of 0.35 to 25 $\mu$m (microns). The above-described method of preparing the PMahy polymers is superior to that described by von Kern et al. using polymethacryloylacid esters. Such esters suitable for reaction with hydrazine hydrate often have a molecular weight of 80,000 Dalton or more, from which it is difficult to obtain a desirably thin film on the waveguide.

Finally, the Fab' fragments were coupled to the free maleimido groups pendant from the polymer-coated surface as follows. The prepared waveguide surface was incubated for 24 hours at 4° C. in a solution containing the Fab' fragments at a concentration of $1.5 \times 10^7$ molar, in a phosphate buffer with 5 mM EDTA (pH 6.0).

EXAMPLE II

Preparation of Waveguide Surface—Avidin-Biotin

This strategy was designed to exploit the very strong binding affinity of biotin for avidin (binding constant of around $10^{-15}$). An avidin coating was readily made by physical adsorption on a silica surface. The Fab' fragments were then conjugated with biotin to form biotin-Fab' conjugates, also referred to as biotinylated Fab' fragments orb-Fab' fragments. The biotin is coupled at specific location (s) on the Fab' fragments. The avidin coated surface is then treated with the b-Fab' fragments, so that the biotin binds to the avidin, thereby immobilizing the Fab' fragment to the surface in a site-specific manner.

In actual experiments, the procedure was as follows. Chromic acid-cleaned silica surfaces were immersed in a solution of $3 \times 10^{-6}$ M (molar) avidin for about 3 hours at room temperature. The surfaces were then washed several times in PBS to remove unabsorbed avidin.

Biotinylated Fab' conjugates were prepared from a solution of Fab' fragments in PBS (0.5–1 mg/ml) by addition of a sufficient amount of 4 mM biotin-HPDP in dimethylformamide to provide a 20-fold molar excess of biotin-HPDP. This mixture was incubated for 90 minutes at room temperature, and biotinylated Fab' fragments (abbreviated b-Fab') were purified by gel permeation chromatography with Sephadex G25 equilibrated in PBS.

An alternate method was used for biotinylating whole antibodies, in which biotin-LC-hydrazide was coupled to oxidized carbohydrate groups in the Fc region of the antibody. Mab, designated 9-40 (a murine monoclonal $IgG_1$ antibody that binds fluorescein), was oxidized by incubation at a concentration of 1–2 mg/ml protein in 10 mM sodium periodate, 0.1 M sodium acetate, pH 5.5, for 20 minutes at about 0° C. Glycerol was then added to a final concentration of 15 mM to quench the reaction, and the mixture incubated a further 5 minutes at 0° C. The oxidized Mab 9-40 was purified by gel filtration chromatography on Sephadex G25 equilibrated with 0.1M sodium acetate buffer, pH 5.5, and then reacted with 5 mM biotin-LC-hydrazide for 2 hours at room temperature with agitation. Unreacted biotin-LC-hydrazide was removed using a Sephadex G25 column equilibrated in PBS.

Avidin-coated surfaces were immersed in a $1.5 \times 10^{-7}$ M solution of b-Fab' fragments for about an hour at room temperature, followed by washing with PBS to remove unbound b-Fab' fragments. Optionally, polyethylene glycol (abbreviated PEG) was coupled to surfaces that were previously coated with the b-Fab' fragments by immersion of the b-Fab'-coated surfaces in a solution of between about $5 \times 10^{-8}$ and $1 \times 10^{-7}$ M PEG. Unbound PEG was removed by washing in PBS.

The density of immobilized Fab' fragments obtained using the avidin-biotin coupling chemistry was about $1.4 \times 10^{-12}$ moles per cm$^2$ (square centimeter).

EXAMPLE III

Preparation of Waveguide Surface—Peg-Type

In this method, the terminal hydroxyl groups of polyethylene glycol (abbreviated PEG) were converted to primary amine or hydrazide groups by reaction with ethylenediamine (abbreviated ED) or hydrazine (abbreviated HZ), respectively, to produce $PEG-ED_2$ or $PEG-HZ_2$. The PEG molecules so modified were then coupled to APS-glutaraldehyde activated silica surfaces. One ED moiety on each $PEG-ED_2$ molecule couples to a free aldehyde group on the silanized-glutaraldehyde-treated waveguide surface. The other ED (or HZ, if $PEG-HZ_2$ is used) is then available to bind to an aldehyde moiety in a capture molecule (binding protein) such as an oxidized antibody or antibody fragment.

Monofunctional (PEG M2000, M5000) or difunctional (PEG 3400, PEG 8000, PEG 18,500) of the indicated molecular weights in Dalton were reacted with p-nitrophenyl chloroformate (abbreviated p-NPC; obtained from Aldrich Chemicals) in solution in benzene. The mixture was agitated at room temperature for about 24 hours. Dry ethyl ether (less than 0.01% water, purchased from J. T. Baker Chemicals) was used to precipitate PEG-(o-NP)$_2$ from solution. The precipitate was vacuum-dried overnight. Between about 50% and about 100% of PEG molecules were converted by this treatment to PEG-Onp, as determined by hydrolysis with 0.1N sodium hydroxide to release the p-nitrophenol groups. The absorbance at 402 nm was determined spectrophotometrically and a molar extinction coefficient of 18400 $M^{-1}$ $cm^{-1}$ used to determine the amount of conversion. The level of conversion depended somewhat on the molecular weight of the PEG of MPEG.

PEG-(o-NP)$_2$ was then dissolved in ethylenediamine and agitated gently for about 3 hours at room temperature. The PEG-(ED)$_2$ was then precipitated by addition of a sufficient amount of dry ethyl ether. The yellow PEG-(ED)$_2$ solution was decolorized by addition of 1 drop of 12N (normal) hydrochloric acid, and the precipitation with ethyl ether repeated twice more. The wet PEG-(ED)$_2$ was dried under vacuum overnight. Alternatively, in place of ethylenediamine, the PEG was derivatized with hydrazine to produce PEG-Hz$_2$.

The modified PEG was coupled to silanized-glutaraldehyde-treated waveguide surfaces prepared as described in Example I. A solution of 24 milligrams (mg) of PEG-ED powder was dissolved in 1.2 milliliters (ml) of 0.15M PBS, pH 7.4, or in the same volume of 11% potassium sulfate-sodium acetate buffer at pH 5.2. The prepared waveguide surfaces were immersed in the PEG-ED solution and incubated at 60° C. for about 24 hours. The procedure using K$_2$SO$_4$-acetate buffer yielded a higher density of PEG molecules attached to the surface than that using PBS buffer. Antibodies or other binding proteins were immobilized to the PEG-coated waveguides as follows. A solution of about 3 mg/ml of antibody was dissolved in 0.15 M sodium acetate buffer, pH 5.2. A solution of equivalent weight of 50 mM sodium metaperiodate (NalO$_4$) was then added, and the reactants were agitated at room temperature for about an hour. Unreacted sodium metaperiodate was removed by passing the reaction mixture through a desalting column (type PD-10 from Pharmacia), which had been pre-equilibrated with the sodium acetate buffer.

The PEG-coated waveguides were then incubated with the oxidized antibody solution in the sodium acetate buffer, pH 5.2, for 3 days at 4° C., then rinsed to remove unbound antibody.

Waveguides prepared by each of the coating procedures of Examples I–III, as well as by prior art random-site coupling methods, were analyzed to determine levels of nonspecific binding relative to total fluorescence and amounts of immobilized antibody and of available binding sites. Comparative results of these analyses are shown in Table 1.

The data in Table I were obtained using fluorescein-BSA (BSA=bovine serum albumen) conjugates with an epitope density of nine (that is, approximately nine fluorescein molecules bound per BSA molecule) and anti-fluorescein antibodies (designated Mab 9-40, or Fab' 9-40 for fragments). A hybridoma cell line secreting this antibody was obtained from Professor E. W. Voss of the University of Illinois at Urbana-Champaign. In these experiments and those whose results are shown in FIGS. 7A, 7B, 8, 9A–9F, and 10A–10D, data acquisition and processing was accomplished using software supplied with the Photometrics Series 200.

Absolute antigen binding was determined by means of radiolabeled tracers or capture molecules. For example, radiolabeled BSA-FL$_9$ was allowed to be coupled with immobilized Fab' fragments for 5 or 60 minutes in phosphate buffer, pH 7.3, at room temperature. The tracer concentration was $1.5 \times 10^{-7}$ M. Three ml per sample of fluorescein-labeled BSA (BSA-FL$_9$) at concentrations ranging from $10^{-10}$ M to $10^{-7}$ M was injected into the flow cell. The injection was performed over a five-minute interval. The spectrum at wavelength of 488 nm was taken and the bulk BSA-FL$_9$ was removed by flushing with PBS buffer. Three more spectra were taken, and the fluorescein peak from 513 to 517 nm was integrated. These values were set versus the log of BSA-FL$_9$ concentration in order to obtain the binding isotherm.

For measurements of radioactivity, the coated silica chips with either immobilized radiolabeled capture molecules or with labeled tracer molecules bound to unlabeled capture molecules were washed thoroughly in a suitable buffer and counted on a gamma counter. $^{125}$I-labeled antibodies or antigens were preferred for the radiolabeling, which was done using the Chloramine-T method (see Greenwood et al., Biochem. J. 89:114–123 (1963)).

The levels of nonspecific absorption of antigen on waveguides prepared by site-specific coupling with avidin-biotin (Example II; Table I, rows 7 and 8 from the top) or hydrogel (Example I; Table I, bottom two rows) were considerably better than most of the prior art coupling methods, being typically 1–3% (Table I). The results also indicated that nonspecific binding to the avidin-coated waveguide was acceptably low for analyte molecule concentrations of less than about $10^{-5}$ M, without a wash step.

The percentage of immobilized molecules that were active (able to bind analyte) was also considerably higher for avidin-biotin and for hydrogel coupling chemistries, being in the range of 50% to 75% for Fabs. The results for IgG capture molecules coupled by heat treatment, acid treatment or by oxidation indicated that only a low percentage of the IgG binding sites were active (Table I, rows 1, 2, 4, 5, 6, 10 from the top).

The row labeled silica-avidin with biotin-PEG represents data obtained with the further refinement of preloading the surface (after attachment of the capture molecules) with biotin-PEG conjugates. This was done to passivate potential nonspecific binding regions. However, the improvement obtained with biotin-PEG preloading was not large.

For the experiments whose results are shown in Tables 11 and m, Fab' fragments derived from a murine anti-human chorionic gonadotropin (anti-hCG) monoclonal IgG antibody were used. The parent monoclonal antibody was purified as described by van Erp et al. *J. Immunol. Methods,* 140:235–241 (1991). This mouse antibody, termed anti-hCG-A, is directed against a portion of the β-subunit of hCG (provided by Organon-Teknika of Boxtel, Netherlands). The whole monoclonal antibody anti-hCG-A was used in the experiments whose results are depicted in FIGS. 7A, 7B, 8, 9A–9F, and 10A–10D. These results also indicated that nonspecific binding to the avidin-coated waveguide was acceptably low for analyte molecule concentrations of less than about $10^{-5}$ M, without a wash step.

The percentage of immobilized molecules that were active (able to bind analyte) was also considerably higher for avidin-biotin and for hydrogel coupling chemistries, being in the range of 50% to 75% for Fabs. The results for IgG capture molecules coupled by heat treatment, acid treatment or by oxidation indicated that only a low percentage of the IgG binding sites were active (Table I, rows 1, 2, 4, 5, 6, 10 from the top).

The row labeled silica-avidin with biotin-PEG represents data obtained with the further refinement of preloading the surface (after attachment of the capture molecules) with biotin-PEG conjugates. This was done to passivate potential nonspecific binding regions. However, the improvement obtained with biotin-PEG preloading was not large.

For the experiments whose results are shown in Tables II and III, Fab' fragments derived from a murine anti-human chorionic gonadotropin (anti-hCG) monoclonal IgG antibody were used. The parent monoclonal antibody was purified as described by van Erp et al., *J. Immunol. Methods*, 140:235–241 (1991). This mouse antibody, termed anti-hCG-A, is directed against a portion of the B-subunit of hCG (provided by Organon-Teknika of Boxtel, Netherlands). The whole monoclonal antibody anti-hCG-A was used in the experiments whose results are depicted in FIGS. 7A, 7B, 8, 9A–9F, and 10A–10D.

F(ab')$_2$ fragments were produced by digestion with pepsin using the procedure described by Grey and Kunkel, "H Chain subgroups of myeloma proteins and normal 7S globulin," *J. Exp. Med.* 120:253–266, 1964. Following digestion, F(ab')$_2$ fragments were reduced to Fab' fragments using dithiothreitol (DTT). Specifically, 33 mg of purified antibody and 1 mg pepsin (Sigma) were dissolved in 0.1 M sodium acetate buffer (pH 4.2) and the digestion was carried out at 37° C. for 16 hours. The digestion was terminated by adjusting the pH of the reaction mixture to 8.0 with 2 M TRIS base. The F(ab')$_2$ fraction was separated by gel permeation chromatography (Superdex Hiload, Pharmacia) using phosphate-buffered saline (PBS), pH 7.7, as eluent. Fab' fragments were prepared by reducing the F(ab')$_2$ fragments (1 mg/ml) with 1.75 mM DTT and 3.5 mM ethylenediamine tetraacetate (EDTA) in 0.17 M.TRIS™ buffer (pH 7.4) for 45 minutes at room temperature. After reduction, excess DTT was removed by gel permeation

TABLE 1

Summary of Solid-Phase Immunoassays using Silica Substrates

| Surface[1] | Antibody[2] | Coupling Chemistry | Total Binding[3] ($\times 10^{-12}$) (moles/cm$^2$) | Absolute Nonspecific Binding ($\times 10^{-12}$) (moles/cm$^2$) | Relative Nonspecific Binding (%) | Immobilized Antibody[5] ($\times 10^{-12}$) (moles/cm$^2$) | Specific Activity[6] (%) |
|---|---|---|---|---|---|---|---|
| Hydrophobic Silica (DDS) | Heat Treated IgG | Random | 0.65 | 0.04 | 6.46 | 3.00 | 21.67 |
| Hydrophobic Silica (DDS) | Acid Treated IgG | Random | 0.67 | 0.07 | 9.70 | 2.20 | 30.45 |
| Hydrophobic Silica (DDS) | Fab' Fragment | Random | 0.37 | 0.25 | 69.00 | 1.30 | 28.46 |
| Silica/APS/GLU | Acid Treated IgG | Random | 0.55 | 0.21 | 38.18 | 3.75 | 14.67 |
| Silica/APS/GLU/PEG | Oxidized IgG | Specific | 0.56 | 0.11 | 19.64 | 2.06 | 27.18 |
| Silica/APS/GLU/PEG | Oxidized IgG | Random | 0.41 | 0.10 | 24.39 | 1.44 | 28.47 |
| Silica/Avidin | Biotin-IgG | Specific | 0.72 | 0.02 | 2.92 | 0.94 | 76.60 |
| Silica/Avidin | Biotin-Fab | Specific | 0.84 | 0.02 | 2.62 | 1.10 | 76.36 |
| Silica/Avidin (with biotin-PEG) | Biotin-Fab | Specific | 0.80 | 0.02 | 1.88 | " | 72.73 |
| Silica/Hydrogel (pre-swollen) | Oxidized IgG | Specific | 0.17 | 0.01 | 6.88 | 7.95 | 2.14 |
| Silica/Hydrogel (pre-swollen) | Fab' Fragment | Specific | 1.51 | 0.03 | 2.03 | 2.76 | 54.71 |

[1]Abbreviations: DDS - dichlorodimethylsilane; APS - aminopropylsilane; GLU - glutaraldehyde; PEG - polyethylene glycol (3400 MW); BSA - bovine serum albumin; IgG - intact immunoglobulin G; Fab' - antigen binding fragment with reactive thiol group; ND - not determined
[2]All immunoassays were performed with an IgG$_1$ monoclonal antibody (9–40) which binds fluorescein.
[3]Amount of $^{125}$I-Fluorescein-BSA which bound to silica substrate.
[4]Amount of $^{125}$I-BSA which bound to silica substrate.
[5]Amount of $^{125}$I-9–40 immobilized on silica substrate.
[6]Percent of immobilized active sites which bound antigen molecules.

TABLE II

Summary of Solid Phase Immunoassays Using Silica Substrates Covered with Hydrogel with Maleimido Reactive Groups

| Antibody | Binding Constant pK$_0$ | Immobilized Antibody ($\times 10^{-12}$ mol/cm$^2$) | Total hCG Binding in 5 min ($\times 10^{-12}$ mol/cm$^2$) | Total hCG Binding in 60 min ($\times 10^{-12}$ mol/cm$^2$) | Antibody Activity (%) | Absolute Nonspecific Binding in 5 min (BSA) ($\times 10^{-12}$ mol/cm$^2$) | Relative Nonspecific Binding in 5 min (BSA) (%) | Absolute Nonspecific Binding in 60 min (BSA) ($\times 10^{-12}$ mol/cm$^2$) | Relative Nonspecific Binding in 60 min (BSA) (%) |
|---|---|---|---|---|---|---|---|---|---|
| Fab' from Anti-hCG-A | 8.85 | 1.39 ± 0.07 | 0.62 ± 0.03 | 0.81 ± 0.03 | 58.3 ± 0.8 | <0.01 | <0.97 | <0.02 | <2.47 |
| Fab' from Anti-hCC-B | 7.89 | 1.29 ± 0.06 | 0.51 ± 0.02 | 0.67 ± 0.03 | 51.9 ± 0.1 | 0.02 ± 0.01 | 3.85 ± 1.81 | 0.04 ± 0.01 | 5.91 ± 1.22 |
| Fab' from Anti-hCG-C | 8.70 | 0.74 ± 0.04 | 0.18 ± 0.01 | 0.41 ± 0.02 | 55.4 ± 0.3 | <0.01 | <6.22 | 0.03 ± 0.01 | 7.21 ± 2.09 |
| Fab' from Anti-hCG-D | 8.00 | 1.45 ± 0.06 | 0.58 ± 0.02 | 0.75 ± 0.03 | 51.4 ± 0.3 | <0.01 | <1.20 | <0.02 | <3.21 |
| Fab' from Mouse IgG | — | 2.50 ± 0.10 | 0.04 ± 0.01 | 0.06 ± 0.02 | 2.4 ± 0.7 | — | — | — | — | chromatography using a Sephadex G-25 column (Pharmacia) equilibrated in 0.1 M sodium phosphate buffer (pH 6.0) containing 5 mM EDTA.

TABLE III

Summary of Solid Phase Immunoassay Using Silica Substrates with Adsorbed Avidin and Biotinylated Fab' Fragments

| Antibody | Immobilized Antibody ($\times 10^{-12}$ mol/cm$^2$) | Total hCG Binding ($\times 10^{-12}$ mol/cm$^2$) | Specific Activity (%) | Absolute Non-specific Binding (BSA) ($\times 10^{-12}$ mol/cm$^2$) | Relative Non-specific Binding (BSA) (%) |
|---|---|---|---|---|---|
| Fab' from Anti-hCG-A | 1.19 ± 0.02 | 1.22 ± 0.01 | 100 ± 5 | 0.05 ± 0.02 | 4.20 ± 0.02 |
| Fab' from Anti-hCG-B | 1.40 ± 0.05 | 1.38 ± 0.07 | 98 ± 9 | 0.05 ± 0.01 | 3.57 ± 0.02 |
| Fab' from Anti-hCG-C | 2.24 ± 0.02 | 1.10 ± 0.03 | 49 ± 3 | 0.05 ± 0.02 | 2.32 ± 0.01 |
| Fab' from Anti-hCG-D | 1.59 ± 0.02 | 1.24 ± 0.01 | 78 ± 2 | 0.05 ± 0.005 | 3.14 ± 0.01 |
| Fab' from Mouse IgG | 1.25 ± 0.02 | 0.03 ± 0.003 | 2.4 ± 0.05 | 0.09 ± 0.03 | 7.20 ± 0.03 |

In the experiments whose results are presented in Tables II and III, the specific binding values were determined using hCG labeled with $^{125}$I, as described for Table I, while $^{125}$I-labeled BSA was used to measure the nonspecific binding. In both Tables II and I, the immobilized antibody was anti-hCG-A.

The fluoroimmunoassays of FIGS. 7A, 7B, 8, 9A–9F, and 10A–10D and Tables I–III were performed using an interfacial fluorometer constructed at the University of Utah. Silica waveguides with the appropriate respective immobilized antigens were placed in the dual-channel flowcell of FIGS. 3A and 3B. The two channels were used for sample and reference measurements, as described with respect to FIGS. 4A–C. The light source was the 514.5 nm emission of an air-cooled argon-ion laser. The laser beam was split into two parallel beams, which were focused with lenses into the two channels of the waveguide. Fluorescence emission was recorded from 520 to 620 nm using a monochromator connected to a computer-controlled CCD camera. The fluorescence spectrum was integrated from 560 nm to 600 nm to improve the signal-to-noise ratio.

Figure 7A:
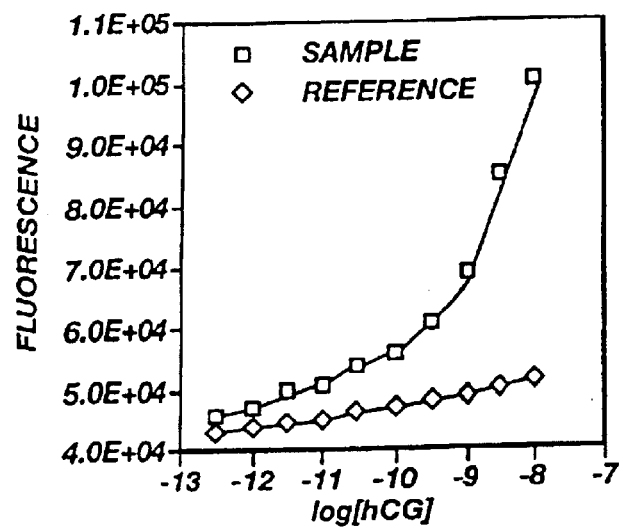
FIG. 7A is a chart depicting fluorescence intensity data from a sandwich fluoroimmunoassay for detecting an antibody and performed with the apparatus of FIG. 1 according to a first assay format.
Figure 7B:
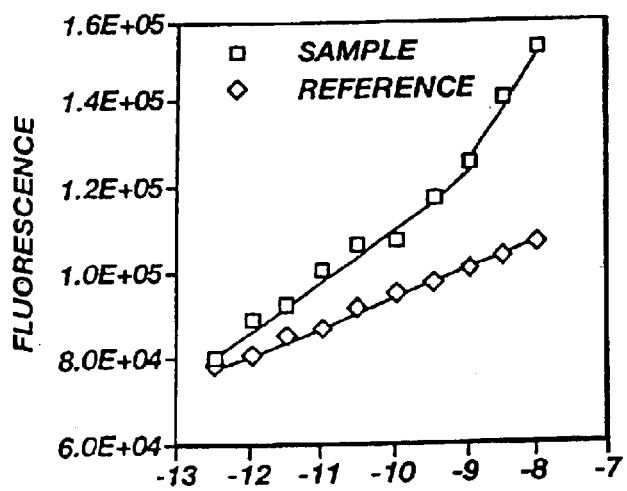
FIG. 7B is a chart depicting data from a sandwich fluoroimmunoassay performed with the apparatus of FIG. 1 according to an alternate assay format.
Figure 8:
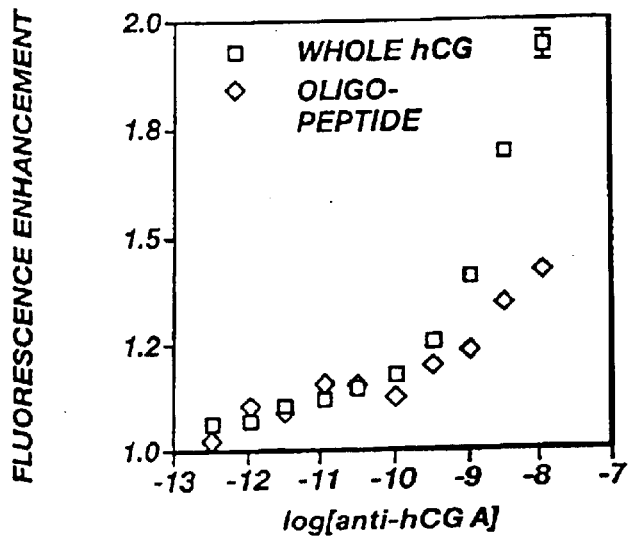
FIG. 8 is a chart comparing the fluorescence enhancement observed with the assay formats of FIGS. 7A and 7B.

FIGS. 7A, 7B and 8 are charts depicting fluorescence intensity data obtained using two alternate formats for performing a fluorescence immunoassay to detect an antibody. In these experiments, the detection of antibodies to human chorionic gonadotropin (abbreviated hCG) was used as a model to determine which format provided the greatest sensitivity. It will be evident that the methods described could be adapted to the detection of any desired antibody in biological fluids such as plasma or serum, for example, the detection of antibodies to proteins of viral and bacterial pathogens, depending only on obtaining the necessary antigen for use as the capture molecule.

For purposes of the tests shown in FIGS. 7A, 7B and 8, the antibody to be detected (the analyte) was chosen to be a monoclonal antibody (designated anti-hCG-A) to an hCG antigen (the latter designated hCG-A). The data of FIG. 7A were obtained with whole hCG molecules serving as the capture molecules (the antigen or analyte binding molecule) in the assay. The data of FIG. 7B were obtained using an oligopeptide constructed to selectively bind the anti-hCG-A antibody as the capture molecules. Oligopeptides suitable for this purpose for any known antigenic analyte molecule analyte can be obtained using the methods of Geysen et al., as disclosed in Patent Publication es. No. WO 86/86487 and U.S. Pat. No. 4,708,871, as well as in the scientific literature. To attach the necessary fluorescent dye, either the N-terminus of the oligopeptide was modified to provide an amino group for amino-reactive dyes, or the C-terminus was modified to provide a cysteine thiol group for thiol-reactive dyes. Preferably also, the complete oligopeptide sequence is of length sufficient that the attached dye is spaced from the binding site by at least two or three residues.

In the experiments of both FIGS. 7A and 7B, the tracer was a goat anti-mouse IgG labeled with tetramethylrhodamine (abbreviated TMR). For both assay formats, the capture molecule was biotinylated as described in Example H and immobilized on an avidin-coated silica substrate. The test antibody, anti-hCG-A, was premixed with the tracer (goat anti-mouse IgG-TMR) in the test solution.

As will be understood by those in the art for a sandwich fluoroimmunoassay, the anti-hCG-A antibody bound to the immobilized capture molecule, and the goat anti-mouse IgG-TMR tracer in turn bound to the mouse anti-hCG-A antibody. In this way, a fluorescent sandwich formed on the substrate surface with the TMR-portion of the tracer molecule being held within the region of evanescent excitation.

The data of FIGS. 7A and 7B were obtained with the following protocol. Different concentrations of anti-hCG-A were premixed with the tracer antibody (concentration fixed at $10^{-8}$ M) and injected into the sample channel. A $10^{-8}$ M concentration of tracer antibody was also injected into the reference channel as a control. The fluorescence intensity of the sample channel was plotted vs. anti-hCG-A concentration and the fluorescence intensity of the reference channel was also plotted on the same set of axes (this is really a plot of the nonspecific binding of the tracer antibody vs. time, since no anti-hCG-A was injected into the reference channel).

FIGS. 7A and 7B show the results for a sandwich assay format following the binding of anti-hCG-A to immobilized hCG and to the oligopeptide, respectively. FIG. 8 shows the corresponding fluorescence enhancements for both cases. The data from FIGS. 7A and 7B were normalized for background fluorescence and replotted as fluorescence enhancement ($F_{sample}/F_{reference}$) versus log analyte concentration. The response curve was similar for both of the immobilized antigens (whole hCG and oligopeptide antigen) over a range of antibody concentrations from $10^{-13}$ M to $10^{-10}$ M. However, whole hCG gave better precision.

It is also evident from FIGS. 7A, 7B and 8 that analyte levels (anti-hCG-A) as low as $10^{-13}$ molar were detectable with the assay. In a further embodiment, the tracer antibody concentration is reduced to $10^{-10}$ M or less. This is expected to reduce background fluorescence due to nonspecific adsorption of the tracer antibody and thereby further improve the sensitivity to $10^{-14}$ M or better.

Figure 9A:
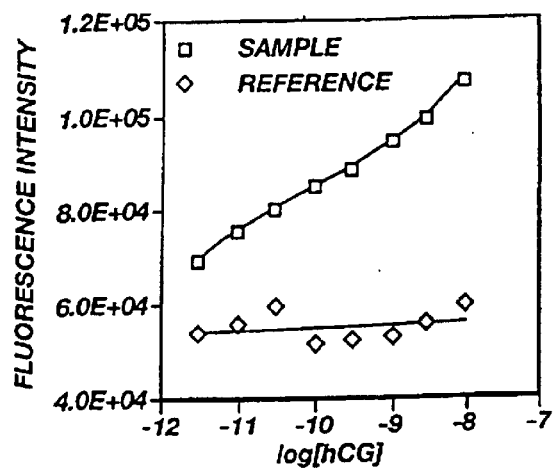
FIGS. 9A–F are charts depicting data from an alternate scheme for a sandwich fluoroimmunoassay for detecting an analyte using a corresponding antibody.
Figure 9B:
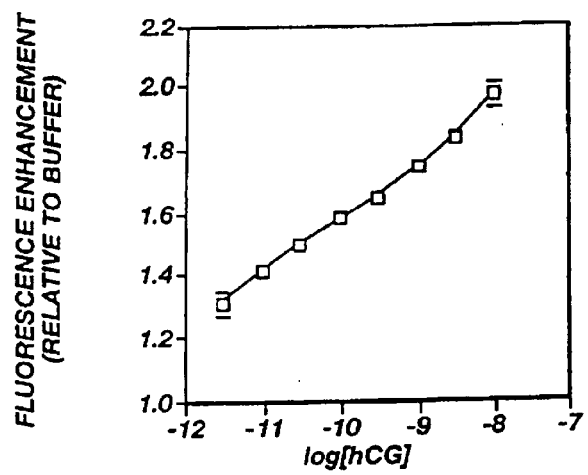
Figure 9C:
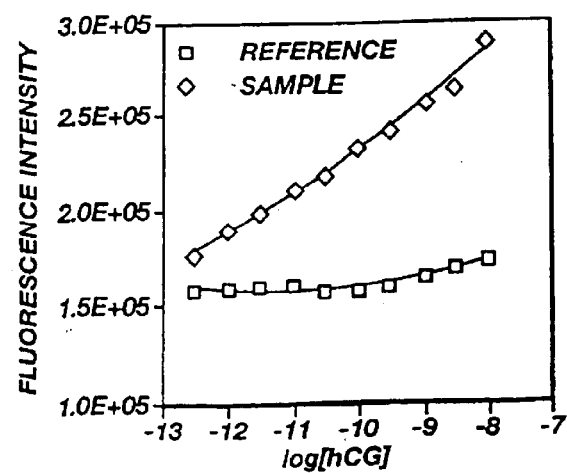

FIGS. 9A–9C depict data obtained using an antibody as the capture molecule to detect an antigen in a sandwich-type assay. As mentioned previously, two different antibodies are employed in a sandwich immunoassay—an immobilized capture antibody and a labeled tracer antibody in solution. Since the capture antibody and the tracer antibody must bind to distinct regions of the antigen, two different monoclonal antibodies which bind to different epitopes on the antigen are typically used in such assays. In addition to the anti-hCG-A, three other monoclonal anti-hCG antibodies (anti-hCG-B, anti-hCG-C and anti-hCG-D, respectively) were obtained from Organon Teknika which bound to different epitopes than did anti-hCG-A. Since only anti-hCG-A is specific to hCG (the others also bind to certain hormones related to hCG), only six of the twelve possible pairwise combinations of antibodies provide strict selectivity for hCG.

Figure 9D:
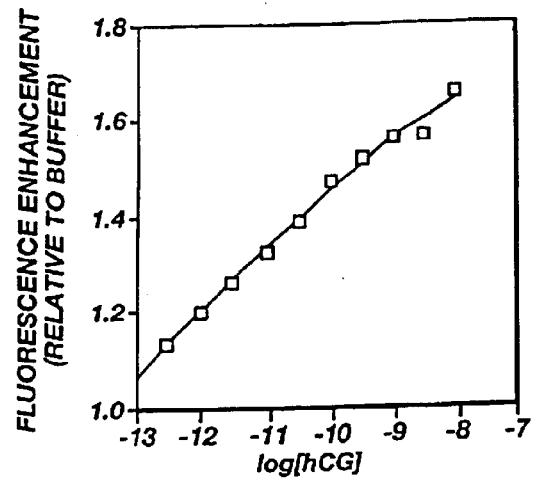
Figure 9E:
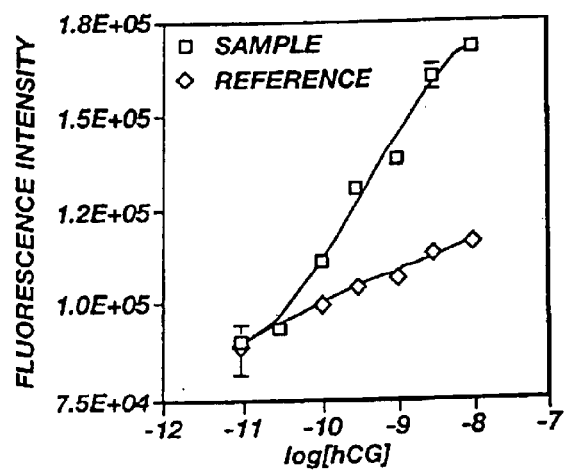
Figure 9F:
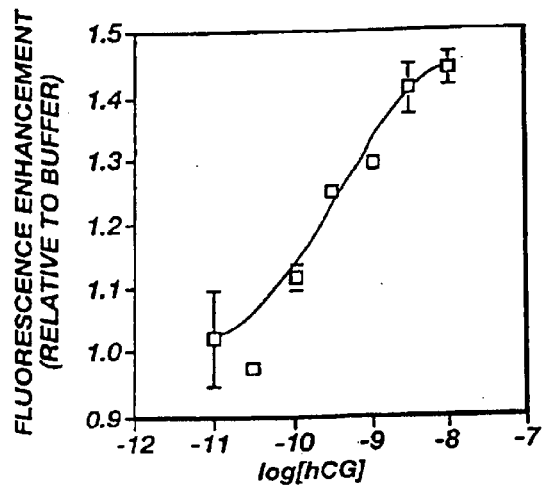

FIGS. 9A–F depict results obtained with different pairwise combinations, with Fab' fragments prepared from anti-hCG-A (Fab'-A) and immobilized to waveguides using the avidin-biotin coupling chemistry. Fab' fragments prepared from anti-hCG-B, anti-hCG-C and anti-hCG-D were labeled with tetramethylrhodamine for use as tracer antibodies (designated Fab'-B, Fab'-C and Fab'-D, respectively). FIGS. 9A and 9B show results with Fab'-B as the tracer molecule. FIGS. 9C, 9D show results obtained using Fab'-C as the tracer molecule. FIGS. 9E and 9F show results obtained using Fab'-D as the tracer molecule. Presently, Fab'-B and Fab'-C are preferred for use as tracers in an hCG assay.

An alternate format used a converse protocol, that is, Fab'-A as the tracer molecule and Fab'-B, -C or -D as the capture molecule. However, the format using Fab'-A as the capture antibody was generally superior in sensitivity. It can be seen from FIG. 9B that hCG concentrations as low as $10^{-12}$ M could be detected by the assay with Fab'-A as capture molecule.

Figure 10A:
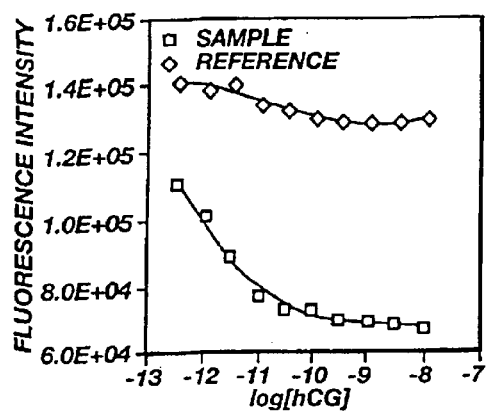
FIGS. 10A–D are charts depicting data from a displacement fluoroimmunoassay performed with the apparatus.
Figure 10B:
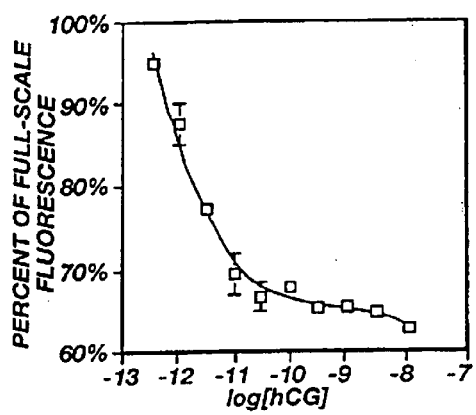
Figure 10C:
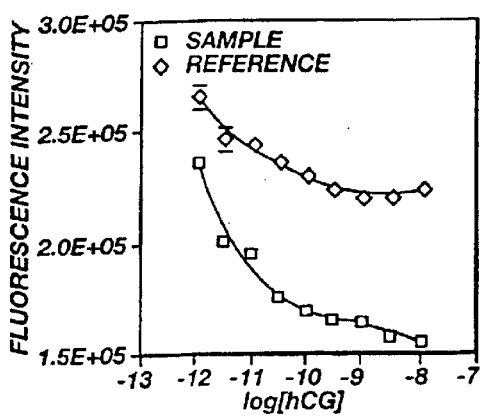
Figure 10D:
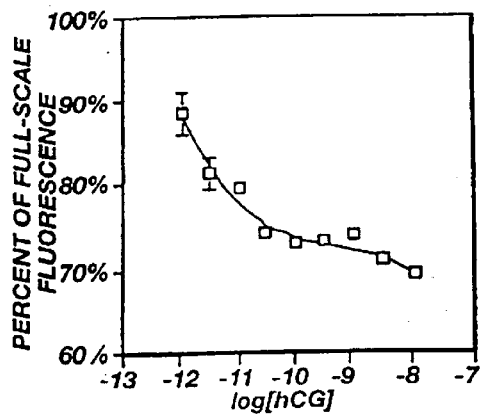

FIGS. 10A–D show data obtained from a competition or displacement assay. Fab'-A fragments were immobilized to waveguides using either the avidin-biotin chemistry (FIGS. 10A, 10B) or the hydrogel coupling chemistry (FIGS. 10C, 10D). The immobilized Fab'-A fragments were preloaded with the tracer oligopeptide at a concentration of $10^{-8}$ M. Increasing concentrations of hCG were added to one channel of the flow cell (sample) and PBS buffer was added to the other (reference). For each coupling chemistry, the raw fluorescence intensities of the sample and reference channels are shown in the panels on the left (10A & 10C) and the percent of full-scale fluorescence (in the absence of hCG) is shown in the panels on the right (10B & 10D). The latter values were normalized for the change in reference fluorescence. Standard errors were plotted for all data points, but in some cases were smaller than the plot marks.

At present, the sandwich immunoassay is preferred for several reasons. First, detection of concentrations down to at least 0.1 picomolar can be demonstrated, as compared to picomolar concentrations for the competitive assay. Also, the instant sandwich immunoassay was capable of detecting concentrations ranging over five logs—from $10^{-8}$ M to $10^{-3}$ M. Thus, a single assay formulation using the sandwich procedure could serve for a variety of applications where different detection limits are required.

A further embodiment of coating chemistry, and one which at present is highly preferred, provides for photo-activated coupling of the binding moiety (Fab fragment, antibody or whatever) to the waveguide surface. By combining the photo activation process with localized irradiation (for example, by masking), it is possible to sequentially couple different binding species to different regions of the waveguide surface. In this way, a waveguide surface patterned with patches, each of a different capture molecule species (preferably Fab' fragments, though Fab fragments and whole antibodies or receptor molecules could be used), can be conveniently produced, without need for walls between the different species. For the present type of evanescent sensor, the elimination of unnecessary walls can significantly improve the sensitivity of the device by reducing background and enhancing evanescent field strength.

In a highly preferred embodiment, the coating chemistry also "passivates" the surface, that is, inhibits nonspecific binding of the fluorescent tracer, and thus reduces the background signal. As described in reference to Examples I–III previously herein, the presently preferred passivating strategy is to coat the waveguide with a very thin layer (preferably no more than about 3 to about 10 nanometers thick) of PEG (polyethylene glycol), having reactive side arms for attachment of the capture molecules.

A presently preferred coating is a type of compound referred to herein as a "block copolymer," comprising at least one hydrophilic block containing polymerized hydrophilic residues (polyethylene oxide, "PEO") adjacent at least one hydrophobic block containing polymerized hydrophobic residues (polypropylene oxide, "PPO"). A subclass of such compounds referred to herein as "triblock copolymers" or "TBCPs," comprises a hydrophobic block flanked by hydrophilic blocks. A series of TBCPs is commercially available from BASF Corporation under the tradename PLURONICS. An example of a presently preferred compound is known generally in the literature as PLURONICS F108 or "PF108"; it has a molecular weight (MW) of about 14,600 and the general formula $(PEO)_x(PPO)_y(PEO)_x$, where x=129 and y=56. In block copolymers, the hydrophobic PPO segment tends to adsorb strongly to plastics including polystyrene, leaving the PEO side-arms in a relatively mobile state. Block copolymers have the general property of inhibiting nonspecific protein adsorption, while providing hydrophilic side chains useful to attach proteins, including Fabs or Fab fragments.

Also, while the present description is primarily with reference to PLURONICS-type compounds, it is within contemplation that other polymeric compounds having hydrophilic segments and hydrophobic segments and offering pendant OH groups for attachment of proteins or photo-activated linkers will be useful. As known in the art, these include SEPHAROSE-type materials and other polysaccharides. Also, block copolymers having polyurethane segments as the hydrophilic block may be useful.

Figure 15:
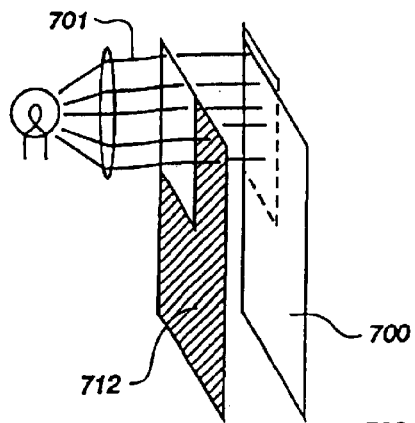
FIG. 15 is a perspective diagram of a photo-masking set-up for producing a waveguide with patches of different Fab' species.
Figure 16:
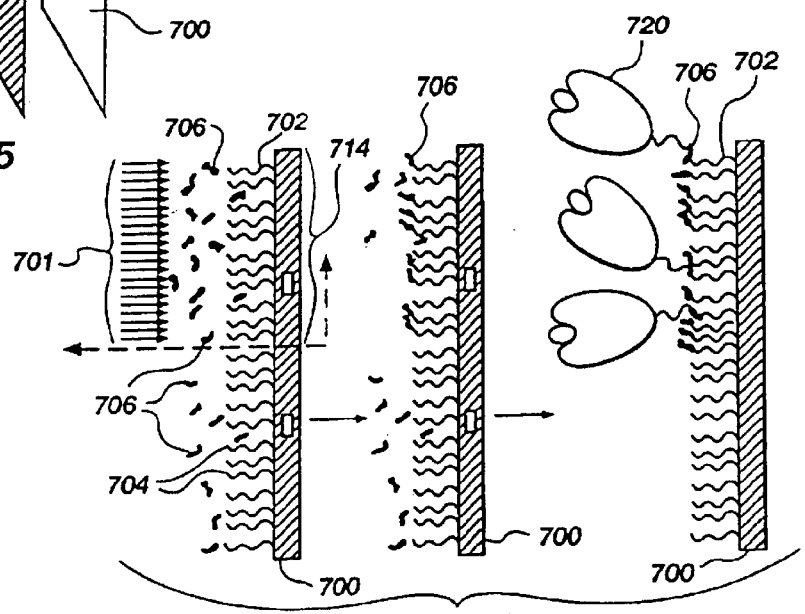
FIG. 16 is a side view of a section of the waveguide surface showing, in schematic form, steps in a process of patterning a waveguide surface with different Fab' species.

Referring to FIG. 16, a general procedure for preparing a patterned polystyrene waveguide is as follows. First, a waveguide surface 700 coated with PF108 molecules 702 is prepared. Next, the free PEO chain ends 704 of the PF108 molecules 702 in a selected region of the waveguide are derivatized in a photo-activated coupling reaction with a photoaffinity crosslinker 706. Suitable crosslinkers are heterobifunctional reagents which have a photo-activatable group conjugated to a reactive functional group such as isothiocyanate, succinimide or maleimide. Upon irradiation with light beam 701 of the appropriate wavelength (generally in the ultraviolet region), the photo-activatable groups of the crosslinker 706 react to covalently bind to the free PEO chain ends 704. A mask 712 (FIG. 15) confines the irradiation to a first region 714 of the waveguide. The result is a waveguide surface having reactive functional groups useful to bind Fab' fragments only in the first region 714. Next, the waveguide surface 700 is incubated with a solution of Fab' fragments of a first species (Fab 1 720 in FIG. 16) for a time sufficient to allow the binding of Fab' fragments to the derivatized region to go to completion. The unreacted Fab' fragments are then washed off, and the process of photo-activated derivatization is repeated for a second region of the waveguide, followed by incubation with a second species of Fab' fragment.

For coupling of Fab' fragments to a waveguide region derivatized with free maleimido groups (procedure of FIG. 16), incubation with a solution of Fab' fragments can be performed substantially as described for the PMahy coating.

Figure 17:
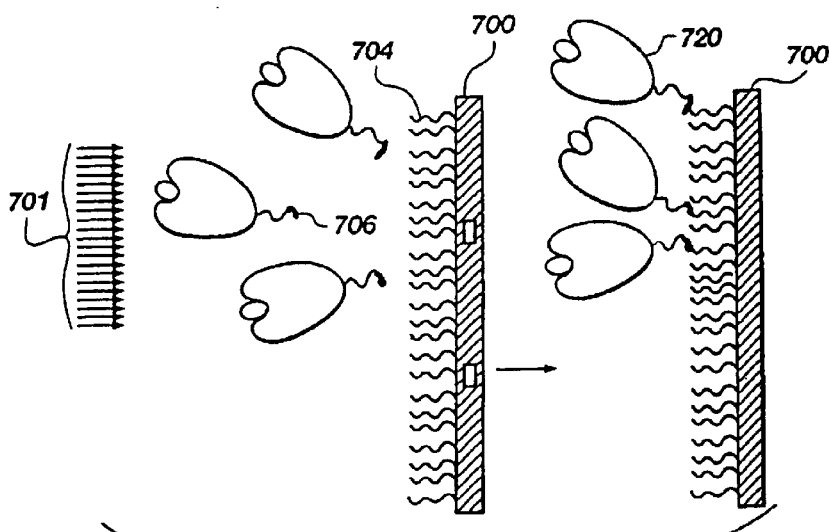
FIG. 17 depicts an alternate embodiment of the patterning process.
Figure 18A:
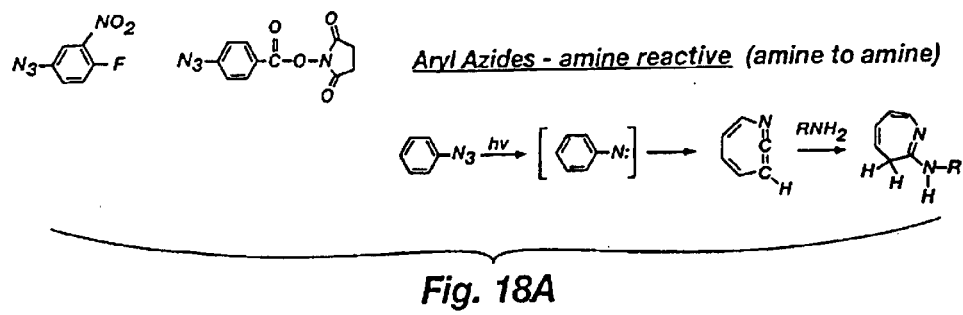
FIGS. 18A, 18B, 18C and 18D show chemical formulas of photo-affinity crosslinkers useful in the invention and partial chemical reactions for photo-coupling the crosslinkers to a base coating.
Figure 18B:
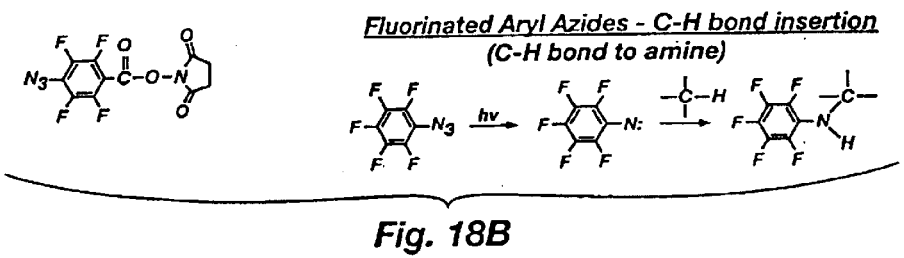
Figure 18C:
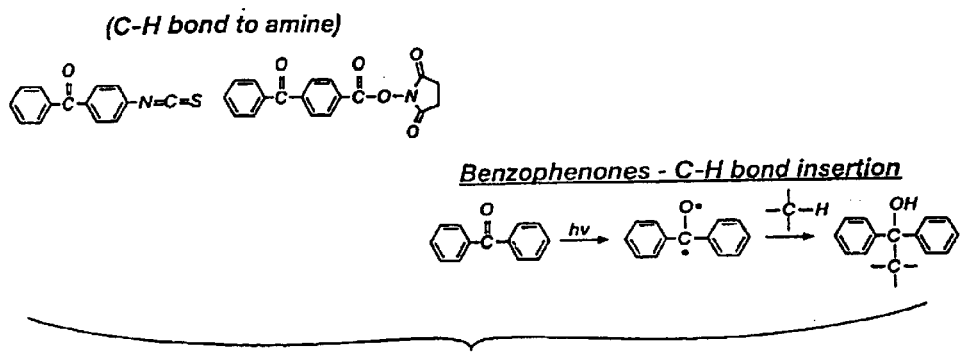
Figure 18D:
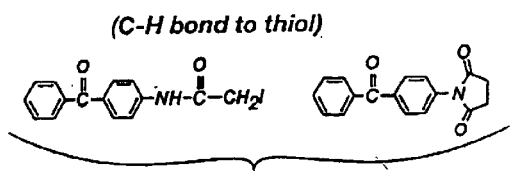

In an alternate embodiment, the Fab' fragments 720 are coupled to the crosslinker 706 before the crosslinker is photo-reacted with the PEO chain ends 704 (FIG. 17). This embodiment is presently preferred because the surfaces thus prepared are capable of binding larger levels of analyte plus tracer per unit area than those prepared according to the protocol of FIG. 16.

Suitable photoaffinity crosslinkers include aryl azides (amine-to-amine linkage), fluorinated aryl azides (C—H bond-to-amine linkage), and benzophenones (C—H bond-to-amine linkage or C—H bond-to-thiol-linkage, depending on the specific compound). Examples of each type are shown in FIGS. 18A–18D, along with the corresponding photo-activated coupling reaction. Presently, benzophenones providing a C—H bond-to-thiol linkage are preferred, as these can be used to achieve site-specific coupling to Fab' fragments. Either the iodoacetamide or the maleimide derivatives of benzophenone ("BPIA" and "BPM," respectively) can achieve this purpose. At present BPM is preferred, as it exhibits a higher degree of specific binding and a lower degree of nonspecific adsorption. This is because the coupling occurs via the C-terminal thiol groups of the Fab' fragments, as described previously herein for the PMahy coating. Other photo-affinity crosslinkers providing free maleimido groups may be equally suitable.

Table IV shows comparative data on the levels of specific binding and nonspecific binding obtained for the crosslinkers BPM vs. BPIA for surfaces which are uncoated or coated with one of four different TBCPs, and for the procedure of FIG. 16 vs. that of FIG. 17. The TBCPs are PF108 and three others designated by the tradenames PPI05, PF68, and PF88, also available from BASF. The respective PEO/PPO/PEO ratios and molecular weights of these compounds are 37/56/37 (PP105, MW=6500), 76/30±6 (PF68, MW=8400), and 104/39/104 (PF88, MW=11,400). As a model system, Fab' fragments derived from the 9-40 anti-fluorescein antibody were used as the capture molecules, with fluorescein-conjugated BSA representing the analyte. The BSA was radioactively labeled. Specific binding was determined as the binding of the fluorescein-BSA-conjugate, while nonspecific binding was determined from binding of native (unconjugated) BSA.

In the photocoupling process, the amount of crosslinker coupled to the PF108 depends on the duration and intensity of the irradiation, the concentration of crosslinker molecules, etc. These variables can easily be tested and optimized to find parameters which will achieve a desired level of crosslinker and/or Fab' protein coupled to the waveguide surface. Generally, a Fab' concentration of about 0.5 mg/ml to about 1 mg/ml and a 20-fold molar excess of crosslinker are useful in the processes of FIGS. 16 and 17.

Table V. contains comparative data concerning the effect of different TBCP coating times on nonspecific binding to PF108-coated polystyrene waveguides. As can be seen, the levels of nonspecific binding achieved were indistinguishable for coating times at least as short as 10 minutes up to at least as long as 24 hours.

From the data in Tables IV and V, it is evident that the degree of nonspecific binding was significantly lower for the PF108 and PP105 coatings than for PF68 and PF88, and with Fab' concentrations of $1.5 \times 10^{-6}$ M. For this reason, PF108 and PP105 are presently preferred BCPs. In general, among TBCP compounds, those exhibiting better resistance to nonspecific binding (and thus presently preferred) are those having PPO segments of length about 45–50 residues or more. Desirably, the level of nonspecific binding should be no more than about 10%, and preferably below about 1%–2%, of the level of specific binding. Alternately, or in addition, it is desirable that the absolute amount of nonspecific binding be in the range below about $5 \times 10^{-14}$ and preferably below about $5 \times 10^{-15}$. Neither the hydrophilic-to-lipophilic balance of the TBCP, the total MW, or the molecular weight ratio of PEO to PPO in the compound appear to be as important as the length of the PPO segment in selecting TBCPs with good efficiency in inhibiting nonspecific binding.

TABLE IV

Specific and Nonspecific Binding of Antigen to Antibodies Immobilized to Polystyrene Using Photo-Affinity Cross-Linking Reagents

| Experiment No. | Pluronics Coating Time | Cross-linker | Fab' Concentration (Molar) | Irradiation Time (min.) | Specific Binding (SB) (mol. cm$^{-2}$) | Nonspecific Binding (NSB) (mol. cm$^{-2}$) | Relative NSB (NSB/SB) (Percent) |
|---|---|---|---|---|---|---|---|
| 1. Fab | None | BPIA-Fab | 5.00e − 6 | 30 | 5.83e − 13 | 6.74e − 14 | 11.6 |
| 2. Fab | None | PS-BPM | 5.00e − 6 | 30 | 9.20e − 13 | 3.71e − 13 | 40.0 |
| 3. Fab | None | BPM-Fab | 5.00e − 6 | 30 | 1.00e − 12 | 7.04e − 14 | 7.0 |
| 4. PF108-Fab | 24 hours | BPIA-Fab | 5.00e − 6 | 30 | 1.01e − 12 | 1.95e − 13 | 19.0 |
| 5. PF108-Fab | 24 hours | PL-BPM | 5.00e − 6 | 30 | 1.74e − 13 | 2.02e − 14 | 11.6 |
| 6. PF108-Fab | 24 hours | BPM-Fab | 5.00e − 6 | 30 | 1.35e − 12 | 1.48e − 13 | 11.0 |
| 7. PF108-Fab | 24 hours | BPM-Fab | 1.00e − 6 | 30 | 3.79e − 13 | 2.08e − 14 | 5.5 |
| 8. PF108-Fab | 24 hours | BPM-Fab | 5.00e − 7 | 30 | 3.40e − 13 | 1.86e − 14 | 5.5 |
| 9. PF108-Fab | 24 hours | BPM-Fab | 1.50e − 6 | 20 | 2.92e − 13 | 3.43e − 15 | 1.2 |
| 10. PF108-Fab | 24 hours | BPM-Fab | 1.50e − 6 | 10 | 3.86e − 13 | 5.66e − 15 | 1.5 |
| 11. PP105-Fab | 24 hours | BPM-Fab | 1.50e − 6 | 10 | 3.66e − 13 | <1e − 15 | <0.3 |
| 12. PP105-Fab | 24 hours | BPIA-Fab | 1.50e − 6 | 10 | 1.07e − 12 | 3.61e − 14 | 3.4 |
| 13. PP105-Fab | 24 hours | BPIA-Fab | 5.00e − 6 | 30 | 6.78e − 13 | 3.87e − 15 | 0.6 |
| 14. Silica—MSil5000-Fab | | BPIA-Fab | 5.00e − 6 | 30 | 1.17e − 13 | 6.66e − 15 | 5.7 |
| 15. Silica—MSil5000-Fab | | BPIA-Fab | 1.50e − 6 | 30 | 1.66e − 13 | Not Determined | — |

In all experiments excepts Nos. 14 & 15, the substrate was a polystyrene surface. In expts. 1–3, there was no PLURONICS coating. In experiments 4–13, the surface was coated for 24 hours with a 4% w/v aqueous solution of the indicated PLURONICS compound. In experiments 1, 3, 4, and 6–15, the Fab' was coupled first to the crosslinker and the complex then photo-crosslinked to the substrate. In experiments 2 and 5, the crosslinker was first photo-coupled to the surface, then incubated with Fab. The concentration of crosslinker used was a 20-fold molar excess of the Fab' concentration.

In addition to the TBCPs discussed above, diblock copolymers of PEO/PPO (DBCPs) will also be effective as waveguide coatings to inhibit nonspecific binding. Here, as with the TBCPs, those compounds having PPO segments of sufficient length, generally greater than about 40–45 residues, will be more effective. At present, TBCPs are preferred over DBCPs, because the PEO blocks are largely responsible for the nonspecific binding-inhibition properties of these compounds.

TABLE V

Effects of Pluronics Coating on the Nonspecific Binding of BSA and Fluorescein-BSA to Polystyrene

| Experiment No. | Pluronics | Pluronics Coating Time | Fluorescein-BSA (mol. cm$^{-2}$) | BSA (mol. cm$^{-2}$) |
|---|---|---|---|---|
| 1. | None | — | 6.05e–12 | 8.37e–13 |
| 2. | F108 | 24 hours | 5.46e–14 | 8.13e–15 |
| 3. | None | — | 1.96 ± 0.04e–12 | 1.53 ± 0.06e–12 |
| 4. | P105 | 24 hours | <1e–15 | <1e–15 |
| 5. | F68 | 24 hours | 1.68 ± 0.36e–13 | 0.91 ± 0.32e–13 |
| 6. | F88 | 24 hours | 1.03 ± 0.30e–13 | 0.32 ± 0.17e–13 |
| 7. | F108 | 10 min | <1e–15 | <1e–15 |
| 8. | F108 | 30 min | <1e–15 | <1e–15 |
| 9. | F108 | 60 min | <1e–15 | <1e–15 |
| 10. | F108 | 180 min | <1e–15 | <1e–15 |
| 11. | F108 | 24 hours | <1e–15 | <1e–15 |

The above-described coupling scheme is very effective with a hydrophobic substrate such as a polystyrene waveguide, but less useful with silica-based substrates such as quartz, glass, and other silicon-based optical materials. Therefore, in an alternate embodiment of the photocoupling method for a waveguide made of a silicon-based material, a silica surface is treated with an undercoating to which a thin top coating of PEG polymer (the protein-resistant component) will effectively adhere. Three schemes for accomplishing this are described in detail herein; all use an undercoating which is a silica-affinic agent having a silyl group free to react with silica. The first scheme is described previously herein in Examples I and III. The second scheme uses avidin to couple a biotinylated-PEG to the surface. This scheme is similar in some respects to Example II, but is modified as described in Example IV. The third scheme is to use an undercoating which makes the silica surface hydrophobic (such as DDS, dichlorodimethylsilane, or DPS, diphenyldichlorosilane), and then to use one of the block copolymers as the top coating. Still another embodiment for use with silica surfaces employs a single coating of a silyl-modified PEG such as methoxy-poly(ethyleneglycol) trimethoxysilane ("PEG-silane") of molecular weight around 3500–to 5000.

The photo-linking process described above with reference to polystyrene surfaces can be adapted for any of these four silica coating schemes, preferably using a benzophenone photo-linker as described in reference to FIGS. 16 and 17 (Example IV). Similar considerations of the relative and/or absolute levels of nonspecific binding apply in selecting preferred undercoating/top coating combinations. Example IV and Table VI describe experiments and results of several such combinations for use with silica-based substrates.

EXAMPLE IV

The specific and nonspecific binding properties of four kinds of coated silica surfaces (silica-MSil(5000), silica APS-Glu-PEG(2000), silica-avidin-biotin-PEG(3400), and silica-DPS-PF108), to which Fab' fragments were photo-crosslinked with BPIA, were evaluated. MSil(5000) is the trimethoxysilane derivative of methoxy-PEG(5000), where PEG(5000) is polyethylene glycol of molecular weight approximately 5000. Diphenylsilane dichloride (DPS) is a generally hydrophobic compound which has an SiCl$_2$ group which can react with the Si—OH bonds in silica.

Silica-MSil(5000) surfaces were prepared by incubating silica chips for 40 min. at 90° C. with a 10% aqueous solution of MSil(5000). Silica-DPS-PF108 surfaces were prepared by immersing the silica chips for 1 h at room temperature in a solution of 10% DPS in toluene. The DPS surfaces were washed with ethanol, then with water, and then immersed in a 4% aqueous solution of PF108 for about 24 hours at room temperature.

Silica-APS-Glu-PEG(2000) surfaces were prepared by incubating silica chips with an aqueous solution of 10% APS at room temperature for 30 minutes. The APS-coated chips were then washed with ethanol and with water, and then immersed in 2.5% aq. solution of glutaraldehyde in bicarbonate buffer, pH 8.0, for 2 hours at room temperature. The chips were washed again, and then reacted with methoxy-PEG(2000) hydrazide in acetate buffer containing 11% K$_2$SO$_4$, pH 5.2, at 60° C. for about 24 hours. Silica-avidin-biotin-PEG(3400) surfaces were prepared by incubating silica chips with avidin (3×10$^{-6}$ M in PBS) at room temperature for 3 hours, then washed with PBS. The avidin-coated chips were then reacted with biotin-PEG(3400) (also 3×10$^{-4}$M in PBS) for 3 hours at room temperature.

TABLE VI

Specific and Nonspecific Binding of Antigen to Silica Surfaces

| Expt. No/ Coating | Concentration (Molar) | Irradiation Time (min.) | Specific Binding (SB) (mol. cm$^{-2}$) | Nonspecific Binding (NSB) (mol. cm$^{-2}$) | Relative NSB (NSB/SB) (Percent) |
|---|---|---|---|---|---|
| 1 MSil [5000] | 5.00e–6 | 30 | 1.2e–13 | 6.7e–15 | 5.7 |
| 2. MSil [5000] | 6.00e–6 | 30 | 3.2e–13 | 2.97e–14 | 9.0 |
| 3. MSil [5000] | 7.00e–6 | 45 | 3.0e–13 | 5.5e–14 | 18.0 |
| 4. MSil [5000] | 7.00e–6 | 45 | 2.7e–13 | 3.3e–14 | 12.0 |
| 5. APS-Glu-PEG [2000] | 6.00e–6 | 30 | 1.1e–13 | 3.3e–14 | 30.7 |
| 6. APS-Glu-PEG [2000] | 6.00e–6 | 30 | 9.6e–13 | 1.9e–14 | 20.0 |
| 7. Av-Bio-PEG [3400] | 6.00e–6 | 30 | 1.1e–13 | 3.2e–15 | 2.8 |
| 8. Av-Bio-PEG [3400] | 6.00e–6 | 30 | 1.0e–13 | 3.2e–15 | 3.2 |
| 9. DPS-PF108 | 6.00e–6 | 30 | 4.5e–13 | 5.4e–14 | 12.0 |
| 10. DPS-PF108 | 6.00e–6 | 30 | 3.0e–13 | 5.7e–14 | 19.0 |
| 11. APS-Glu-PEG [2000] | 6.00e–6 | 30 | NA | 3.0e–14 | NA |
| 12. APS-Glu-PEG [2000] | 6.00e–6 | 30 | NA | 9.8e–15 | NA |
| 13. Au-Bio-PEG [3400] | 6.00e–6 | 30 | NA | 2.9e–15 | NA |
| 14. Au-Bio-PEG [3400] | 6.00e–6 | 30 | NA | 1.8e–15 | NA |
| 15. DPS-PF108 | 6.00e–6 | 30 | NA | 7.05e–14 | NA |
| 16. DPS-PF108 | 6.00e–6 | 30 | NA | 7.04e–14 | NA |

Silica chips were prepared as described in Example IV. In experiments 1–10, both specific and nonspecific binding of antigen were measured for surfaces having a Fab' fragment of the 9–40 antibody immobilized by BPIA crosslinking to the indicated coating. The procedure of FIG. 17 (Fab'-BPIA conjugates prepared, then photo-linked to coating) was used. In experiments 11–16, only nonspecific binding to coated surfaces(no BPIA or Fab') was measured for each type of coating.

Fab'-photo-crosslinker conjugates were prepared by reacting Fab' fragments (of the 9–40 antibody) with benzophenone iodoacetamide (BPIA) at a molar ratio of 1(Fab'):20

(BPIA) in Hepes buffer, pH 7.4, at room temperature for 2 hours. The conjugated Fab' fragments were separated and purified by passing the reaction mixture through a PD-10 column in the same buffer to remove the excess BPIA. The photo-linking reaction was performed by irradiating the prepared silica chips in a solution of Fab'-BPIA conjugates in a quartz cuvette with 295 nm light at room temperature for 30 minutes; the output of the light source was measured to be approximately 4.7 milliwatts per $cm^2$. Specific and non-specific binding were determined as for the data of Tables IV and V.

The results presented in Table VI indicate that of the above coating chemistries and using BPIA as the photo-linker, the avidin-biotin/PEG(3400) combination gave the best results, and the MSil(5000) gave the next best results.

It is also possible to use photo-crosslinking of capture molecules on a silica surface coated with APS only, by using an aryl azide (FIGS. 18A–18D) as a bridge between the amino group in APS and the amine groups in the antibody (or other protein-type capture molecule). However, this protocol does not provide site-specific attachment of the antibody to the waveguide surface, since antibodies have plural amine groups, nor does it render the silica surface protein-resistant and, therefore, is presently considered much less desirable, The patterning processes described above require a suitable light source for localized crosslinker photo-activation. As described above, localized photo-coupling may be performed with an incoherent light source such as a xenon lamp with lens and a mask (FIG. 15). A mercury vapor lamp with a 300 nm bandpass filter and a mask are another example of a useful incoherent light source. Alternatively, a coherent UV light source such as an argon ion laser may be used in combination with a translation stage. In the latter embodiment, a mask may or may not be needed to achieve the desired localized irradiation.

While many of the preceding experimental examples and results were obtained using hCG antigen/anti-hCG antibody and fluorescein/anti-fluorescein antibody systems, it will be understood by those skilled that the apparatus and the biosensor, as well as the site-specific waveguide-coupling methods and assay formats, all are applicable to assays for any antigen or antibody for which the requisite reagents such as appropriate capture molecules can be obtained, without undue experimentation. It will further be understood that while tetramethyl-rhodamine, fluorescein, and cyanine dyes are specifically mentioned as useful for labeling of tracer molecules, the apparatus and methods can also be useful with other fluorescent dyes capable of being conjugated to the desired tracer molecule.

Also, while the novel subject matter of this application is described herein primarily with respect to the apparatus in which excitation is by an evanescent field, the evanescent field is produced by directing a light beam into the edge or end of a waveguide, and the resulting fluorescence is directly collected from the evanescent zone (e.g., not via evanescent coupling back into the waveguide), the usefulness of many elements of both the optical and chemical portions of the subject matter is not so limited. Many elements in the instant subject matter will also be useful in alternate configurations of evanescent-light biosensors. One such alternate configuration is that in which the tracer molecules are excited by a non-evanescent light source, and the fluorescence is collected as evanescent light that propagates through the waveguide and is collected at the edge or end. Another such alternate configuration provides evanescent field excitation via a waveguide illuminated from the edge or end thereof, with collection of fluorescent light by evanescent penetration back into the waveguide.

It will further be recognized that various modifications and substitutions may be made to the apparatus and the biosensor as described herein, without departing from the concept and scope of the invention.

What is claimed is:

1. An assay system, comprising:
    a receptor for receiving a sample solution that may include at least one selected analyte;
    a reaction zone comprising at least a portion of said receptor or in fluid communication with said receptor, said reaction zone including at least one reagent configured to produce a reaction mixture with said sample solution;
    at least one detection zone in fluid communication with said reaction zone and configured to receive at least a portion of said reaction mixture transported from said reaction zone, said at least one detection zone is carried upon a surface of at least a portion of a waveguide; and
    a detector oriented to receive signals from said at least one detection zone and configured to sense a physically detectable change in said at least one detection zone, said physically detectable change correlating with at least one of an absence, a presence, and an amount of said at least one selected analyte in said sample solution, said detector configured to generate a signal correlating with at least one of said absence, said presence, and said amount.

2. The assay system of claim 1, wherein said at least said portion of said waveguide comprises a substantially planar structure.

3. The assay system of claim 1, wherein said waveguide comprises a planar waveguide.

4. The assay system of claim 1, wherein said detector is oriented to detect light emitted from said at least one detection zone.

5. The assay system of claim 4, wherein said detector is oriented to detect light emitted through at least said portion of said waveguide.

6. The assay system of claim 4, wherein said detector is positioned within a cone of collection angles having an axis oriented substantially orthogonal to the plane of at least said portion of said waveguide.

7. The assay system of claim 1, comprising a plurality of detection zones.

8. The assay system of claim 7, wherein said plurality of detection zones is carried upon a surface of at least said portion of said waveguide.

9. The assay system of claim 8, wherein detection zones of said plurality of detection zones are positioned at discrete locations from one another on said surface.

10. The assay system of claim 9, wherein said discrete locations are arranged in an array.

11. The assay system of claim 7, wherein at least two of said plurality of detection zones comprise different capture molecules capable of reacting with different analytes.

12. The assay system of claim 1, wherein said reaction mixture comprises a reaction product including said at least one selected analyte, said at least one reagent bound thereto, and a physically detectable label on said at least one reagent.

13. The assay system of claim 12, wherein said physically detectable label emits light when excited.

14. The assay system of claim 13, further comprising:
    a source of electromagnetic energy of at least one wavelength capable of exciting said physically detectable label.

15. The assay system of claim 14, wherein said electromagnetic energy comprises an evanescent field.

16. The assay system of claim 1, further comprising:
a display for illustrating data representative of said amount of said at least one selected analyte in said sample solution.

17. An assay system, comprising:
a receptor for receiving a sample solution that may include at least one selected analyte;
a reaction zone comprising at least a portion of said receptor or in fluid communication with said receptor, said reaction zone including at least one reagent configured to produce a reaction mixture with said sample solution, said reaction mixture comprising a reaction product including said at least one selected analyte, said at least one reagent bound thereto, and a physically detectable label that emits light when excited by an evanescent field;
at least one detection zone in fluid communication with said reaction zone and configured to receive at least a portion of said reaction mixture transported from said reaction zone;
a source configured and oriented to cause the generation of said evanescent field at said at least one detection zone; and
a detector oriented to receive signals from said at least one detection zone and configured to sense a physically detectable change in said at least one detection zone, said physically detectable change correlating with at least one of an absence, a presence, and an amount of said at least one selected analyte in said sample solution, said detector configured to generate a signal correlating with at least one of said absence, said presence, and said amount.

18. The assay system of claim 17, wherein said at least one detection zone is carried by a substantially planar structure.

19. The assay system of claim 18, wherein said at least one detection zone is carried upon a surface of said substantially planar structure.

20. The assay system of claim 19, wherein said substantially planar structure comprises at least a portion of a planar waveguide.

21. The assay system of claim 18, wherein said detector is oriented to detect light emitted from said at least one detection zone.

22. The assay system of claim 21, wherein said detector is oriented to detect light emitted through said substantially planar structure.

23. The assay system of claim 21, wherein said detector is positioned within a cone of collection angles having an axis oriented substantially orthogonal to the plane of said substantially planar structure.

24. The assay system of claim 17, comprising a plurality of detection zones.

25. The assay system of claim 24, wherein at least two of said plurality of detection zones comprise different capture molecules capable of reacting with different analytes.

26. The assay system of claim 24, wherein said plurality of detection zones is carried upon a surface of a substantially planar structure.

27. The assay system of claim 26, wherein detection zones of said plurality of detection zones are positioned at discrete locations from one another on said surface.

28. The assay system of claim 27, wherein said discrete locations are arranged in an array.

29. The assay system of claim 28, wherein said substantially planar structure comprises a planar waveguide.

30. The assay system of claim 17, further comprising:
a display for illustrating data representative of said amount of said at least one selected analyte in said sample solution.

* * * * *